United States Patent
Doihara et al.

(10) Patent No.: US 11,667,724 B2
(45) Date of Patent: Jun. 6, 2023

(54) ANTI-HUMAN CEACAM5 ANTIBODY FAB FRAGMENT

(71) Applicant: ASTELLAS PHARMA INC., Tokyo (JP)

(72) Inventors: Hitoshi Doihara, Tokyo (JP); Kazunori Hirayama, Tokyo (JP); Hiroki Shirai, Tokyo (JP)

(73) Assignee: ASTELLAS PHARMA INC., Tokyo (JP)

( * ) Notice: Subject to any disclaimer, the term of this patent is extended or adjusted under 35 U.S.C. 154(b) by 498 days.

(21) Appl. No.: 16/628,975

(22) PCT Filed: Jul. 6, 2018

(86) PCT No.: PCT/JP2018/025618
§ 371 (c)(1),
(2) Date: Jan. 6, 2020

(87) PCT Pub. No.: WO2019/009388
PCT Pub. Date: Jan. 10, 2019

(65) Prior Publication Data
US 2020/0123270 A1   Apr. 23, 2020

(30) Foreign Application Priority Data
Jul. 7, 2017   (JP) .............................. JP2017-133698

(51) Int. Cl.
*A61K 51/10*   (2006.01)
*C07K 16/30*   (2006.01)
*G01N 33/574*   (2006.01)

(52) U.S. Cl.
CPC ...... *C07K 16/3007* (2013.01); *A61K 51/1093* (2013.01); *A61K 51/1096* (2013.01);
(Continued)

(58) Field of Classification Search
None
See application file for complete search history.

(56) References Cited

U.S. PATENT DOCUMENTS 8,623,367 B2   1/2014   Momm et al.
2002/0146750 A1   10/2002   Hoogenboom et al.
(Continued)

FOREIGN PATENT DOCUMENTS

CA   3115747 A1   4/2020
CN   102482701 B   5/2015
(Continued)

OTHER PUBLICATIONS

Akizawa et al., Renal brush border enzyme-cleavable linkages for low renal radioactivity levels of radiolabeled antibody fragments, Bioconjugate Chem., 24(2):291-299 (2013).
(Continued)

*Primary Examiner* — Aurora M Fontainhas
(74) *Attorney, Agent, or Firm* — Marshall, Gerstein & Borun LLP

(57) ABSTRACT

Provided are an anti-human CEACAM5 antibody Fab fragment expected to be useful in the diagnosis of a cancer, particularly, the diagnosis of colorectal cancer, breast cancer, lung cancer, thyroid gland cancer or a cancer resulting from the metastasis thereof, and a diagnosis approach using a conjugate comprising the Fab fragment. The present invention provides an anti-human CEACAM5 antibody Fab fragment comprising a heavy chain fragment comprising a heavy chain variable region consisting of the amino acid sequence represented by amino acid positions 1 to 121 of SEQ ID NO: 2, and a light chain comprising a light chain variable region consisting of the amino acid sequence rep-
(Continued)

resented by amino acid positions 1 to 112 of SEQ ID NO: 4, and a conjugate comprising the Fab fragment.

35 Claims, 2 Drawing Sheets

Specification includes a Sequence Listing.

(52) U.S. Cl.
CPC ..... *G01N 33/574* (2013.01); *G01N 33/57492* (2013.01); *C07K 2317/55* (2013.01)

(56) References Cited

U.S. PATENT DOCUMENTS

| | | |
|---|---|---|
| 2005/0118167 A1 | 6/2005 | Okada et al. |
| 2005/0244333 A1 | 11/2005 | Yazaki et al. |
| 2008/0069816 A1 | 3/2008 | Yazaki et al. |
| 2009/0081213 A1 | 3/2009 | Chevrier et al. |
| 2010/0034825 A1 | 2/2010 | Clausen et al. |
| 2010/0111856 A1 | 5/2010 | Gill et al. |
| 2011/0236398 A1 | 9/2011 | Momm et al. |
| 2012/0040375 A1 | 2/2012 | Nishimura et al. |
| 2012/0128676 A1 | 5/2012 | Danielczyk et al. |
| 2012/0219503 A1 | 8/2012 | Kumar et al. |
| 2012/0251529 A1 | 10/2012 | Hofer et al. |
| 2012/0294859 A1 | 11/2012 | Goletz et al. |
| 2012/0328514 A1 | 12/2012 | Cesati et al. |
| 2013/0045543 A1 | 2/2013 | Nishimura et al. |
| 2013/0123471 A1 | 5/2013 | Yang et al. |
| 2014/0212408 A1 | 7/2014 | Hofer et al. |
| 2015/0005474 A1 | 1/2015 | Goletz et al. |
| 2015/0056134 A1 | 2/2015 | Sawada et al. |
| 2015/0078997 A1 | 3/2015 | Cesati et al. |
| 2016/0011217 A1 | 1/2016 | Matsumura et al. |
| 2016/0108131 A1 | 4/2016 | Berne et al. |
| 2016/0229923 A1 | 8/2016 | Hofer et al. |
| 2017/0198056 A1 | 7/2017 | Nishimura et al. |
| 2018/0022817 A1 | 1/2018 | Berne et al. |
| 2018/0079827 A1 | 3/2018 | Hofer et al. |
| 2018/0221512 A1 | 8/2018 | Yazaki et al. |
| 2019/0091353 A1 | 3/2019 | Arano et al. |
| 2019/0185583 A1 | 6/2019 | Hofer et al. |
| 2019/0269804 A1 | 9/2019 | Morinaka et al. |
| 2020/0102401 A1 | 4/2020 | Berne et al. |
| 2020/0123270 A1 | 4/2020 | Doihara et al. |
| 2020/0268913 A1 | 8/2020 | Arano et al. |
| 2021/0355233 A1 | 11/2021 | Suemitsu et al. |

FOREIGN PATENT DOCUMENTS

| | | |
|---|---|---|
| CN | 109952375 A | 6/2019 |
| EP | 2347769 A1 | 7/2011 |
| EP | 2351777 A1 | 8/2011 |
| EP | 2565268 A1 | 3/2013 |
| EP | 2567982 A1 | 3/2013 |
| EP | 3543337 A1 | 9/2019 |
| EP | 3795590 A1 | 3/2021 |
| EP | 3865154 A1 | 8/2021 |
| EP | 3909606 A1 | 11/2021 |
| EP | 3909608 A1 | 11/2021 |
| JP | 2010-505775 A | 2/2010 |
| JP | 2012-511540 A | 5/2012 |
| JP | 2012-532868 A | 12/2012 |
| JP | 2013-500703 A | 1/2013 |
| JP | 2013-505702 A | 2/2013 |
| JP | 2013-510093 A | 3/2013 |
| JP | 2013-517487 A | 5/2013 |
| JP | 2016-506370 A | 3/2016 |
| JP | 2016-534735 A | 11/2016 |
| KR | 10-2019-0078573 A | 7/2019 |
| TW | 201920273 A | 6/2019 |
| WO | 2000/66160 A1 | 11/2000 |
| WO | 2001/75110 A2 | 10/2001 |
| WO | 2005/086875 A2 | 9/2005 |
| WO | WO-2005/086875 A2 | 9/2005 |
| WO | 2007/019232 A2 | 2/2007 |
| WO | 2008/040362 A2 | 4/2008 |
| WO | 2010/050528 A1 | 5/2010 |
| WO | 2010/066762 A1 | 6/2010 |
| WO | 2011/005322 A2 | 1/2011 |
| WO | 2011/012309 A1 | 2/2011 |
| WO | 2011/034660 A1 | 3/2011 |
| WO | 2011/037271 A1 | 3/2011 |
| WO | 2011/056983 A1 | 5/2011 |
| WO | 2011/089004 A1 | 7/2011 |
| WO | 2011/135869 A1 | 11/2011 |
| WO | 2012/015912 A1 | 2/2012 |
| WO | 2012/117002 A1 | 9/2012 |
| WO | 2013/081091 A1 | 6/2013 |
| WO | 2014/079886 A1 | 5/2014 |
| WO | WO-2014/079886 A1 | 5/2014 |
| WO | WO-2014/133093 A1 | 9/2014 |
| WO | 2014/177568 A1 | 11/2014 |
| WO | 2015/094900 A1 | 6/2015 |
| WO | WO-2015/053871 A4 | 7/2015 |
| WO | 2015/157286 A1 | 10/2015 |
| WO | 2015/166934 A1 | 11/2015 |
| WO | 2016/073915 A1 | 5/2016 |
| WO | 2016/130726 A1 | 8/2016 |
| WO | 2017/150549 A1 | 9/2017 |
| WO | 2018/092885 A1 | 5/2018 |
| WO | 2019/009388 A1 | 1/2019 |
| WO | 2019/065774 A1 | 4/2019 |
| WO | 2019/221269 A1 | 11/2019 |
| WO | 2020/075746 A1 | 4/2020 |
| WO | 2020/145227 A1 | 7/2020 |
| WO | 2020/145228 A1 | 7/2020 |

OTHER PUBLICATIONS

Arano et al., Chemical design of radiolabeled antibody fragments for low renal radioactivity levels, Cancer Research, 59(1):128-134 (1999).

Chevallier et al., BCR-ABL1 molecular remission after 90Y-epratuzumab tetraxetan radioimmunotherapy in CD22+ Ph+ B-ALL: proof of principle, European Journal of Hematology, 91(6):552-556 (2013).

Giannini et al., Synthesis and preliminary in vitro evaluation of DOTA-Tenatumomab conjugates for theranostic applications in tenascin expressing tumors, Bioorganic Med. Chem., 27(15):3248-3253 (2019).

International Application No. PCT/JP19/039793, International Preliminary Report on Patentability received for dated Apr. 22, 2021.

International Application No. PCT/JP2017/041486, International Preliminary Report on Patentability, dated May 31, 2019.

International Application No. PCT/JP2017/041486, International Search Report and Written Opinion, dated Feb. 13, 2018.

International Application No. PCT/JP2019/019663, International Preliminary Report on Patentability, dated Nov. 26, 2020.

International Application No. PCT/JP2019/019663, International Search Report and Written Opinion, dated Aug. 13, 2019.

International Application No. PCT/JP2020/000036, International Search Report and Written Opinion, dated Mar. 24, 2020.

International Application No. PCT/JP2020/000037, International Search Report and Written Opinion, dated Apr. 7, 2020.

Li et al., Reduction of kidney uptake in radiometal labeled peptide linkers conjugated to recombinant antibody fragments. Site-specific conjugation of DOTA-peptides to a Cys-diabody, Bioconjugate Chem., 13(5):985-995 (2002).

Russian Office Action Patent Application No. 2019118653 dated Aug. 20, 2021.

Study to Evaluate the Safety and Preliminary Efficacy of 177Lu-OPS201 in NETs, ClinicalTrials.govIdentifier_NCT02592707 (2015).

Tsai et al., Metabolism and renal clearance of 111In-labeled DOTA-conjugated antibody fragments, Bioconjugate Chem., 12(2):264-270 (2001).

Uehara et al., (67/68)Ga-labeling agent that liberates (67/68)Ga-NOTA-methionine by lysosomal proteolysis of parental low molecu-

(56) References Cited

OTHER PUBLICATIONS lar weight polypeptides to reduce renal radioactivity levels, Bioconjugate Chem., 25(11):2038-2045 (2014).
Uehara et al., A Gallium-67/68-Labeled Antibody Fragment for Immuno-SPECT/PET Shows Low Renal Radioactivity Without Loss of Tumor Uptake, Clin. Cancer Res., 24(14):3309-3316 (2018).
Uehara et al., Design, synthesis, and evaluation of [188Re]organorhenium-labeled antibody fragments with renal enzyme-cleavable linkage for low renal radioactivity levels, Bioconjugate Chem., 18(1):190-198 (2007).
Wu et al., Biodistribution and catabolism of Ga-67-labeled anti-Tac dsFv fragment, Bioconjugate Chem., 8(3):365-369 (1997).
Yarilin, Fundamentals of Immunology: Textbook.—M: Medicine, 608s, p. 171 second paragraph, pp. 172-173 (1999).
Oppposition dated Dec. 15, 2021 against corresponding Colombian Application No. NC2021/0010115, 32 pages (16 pages of English Translation and 16 pages of Original Document).
Akizawa et al., Renal uptake and metabolism of radiopharmaceuticals derived from peptides and proteins, Advanced Drug Deliver Reviews, 60:1319-1328 (2008).
CEA-SCAN (Registered), For the Preparation of Technetium Tc 99m Arcitumomab, Sterile, Non-Pyrogenic, Lyophilized Powder for Intravenou s Use Only, URL https://pharmacyce.unm.edu/nuclear_program/neolibrary/libraryfiles/package_inserts/cea-scan.pdf, 11 pages.
Danielczyk et al., PankoMab: a potent new generation anti-tumour MUCI antibody, Cancer Immunol. Immunother., 55(11):1337-1347 (2006).
Extended European search Report European Application No. 17870672.7, European Search Report, dated Jul. 6, 2020.
International Application No. PCT/JP19/039793, International Search Report and Written Opinion, dated Dec. 24, 2019.
International Application No. PCT/JP2017/041486, International Search Report, dated Feb. 13, 2018.
International Application No. PCT/JP2018/025618, International Preliminary Report on Patentability, dated Jan. 16, 2020.
International Application No. PCT/JP2019/019663, International Search Report, dated Aug. 13, 2019.
Kiyoshi et al., Affinity improvement of a therapeutic antibody by structure-based computational design: generation of electrostatic interactions in the transition state stabilizes the antibody-antigen complex, PLOS ONE, 9(1):1-9, e87099, (2014).
Lavrsen et al., Aberrantly glycosylated MUCI is expressed on the surface of breast cancer cells and a target for antibody-dependent cell-mediated cytotoxicity, Glycoconj. J., 30(3):227-236 (2013).
Perk et al., p-Isothiocyanatobenzyl-desferrioxamine: a new bifunctional chelate for facile radiolabeling of monoclonal antibodies with zirconium-89 for immuno-PET imaging, Eur. J. Nucl. Med. Mol. Imaging, 37(2):250-259 (2010).
Rosenthal et al., Sensitivity and specificity of cetuximab-IRDyeSOOCW to identify regional metastatic disease in head and neck cancer, Clinical Cancer Research, 23(16):4744-4752 (2017).
Shirai et al., High-resolution modeling of antibody structures by a combination of bioinformatics, Expert Knowledge, and Molecular Simulations, 82(8):1624-1635 (2014).
Van De Watering et al., Zirconium-89 labeled antibodies: a new tool for molecular imaging in cancer patients, BioMed. Research International, Article ID 203601:1-13 (2014).
Taiwanese Office Action dated May 27, 2022 in Taiwanese Patent Application No. 107123231 12 pages (6 pages of English Translation and 6 pages of Original Document).

Almagro et al., "Humanization of antibodies", Frontiers In Bioscience, Albertson, NY, US, vol. 13, pp. 1619-1633 (2008).
Extended European Search Report in EP Application No. 19804452.1 dated Apr. 5, 2022.
Gold et al., "Combined 90Yttrium-dota-labeled PAM4 Antibody Radioimmunotherapy and Gemcitabine Radiosensitization for the Treatment of a Human Pancreatic Cancer Xenograft", International Journal of Cancer, vol. 109, No. 4, pp. 618-626 (2004).
Cheng, "99mTc-Arcitumomab", [online], Update: Mar. 17, 2008, Molecular Imaging and Contrast Agent Database, [searched on May 17, 2017], internet URL:https://www.ncbi.nlm.nih.gov/books/NBK23676/.
Hughes et al., Use of carcinoembryonic antigen radioimmunodetection and computed tomography for predicting the resectability of recurrent colorectal cancer, Ann. Surg., 226:621-31 (1997).
Li et al., A Versatile Bifunctional Chelate For Radiolabeling Humanized Anti-CEA Antibody With In-111 And Cu-64 At Either Thiol Or Amino Groups: PET Imaging Of CEA-Positive Tumors With Whole Antibodies, Bioconjug. Chem. 19:89-96 (2008).
Willkomm et al., FDG PET and immunoscintigraphy with 99mTc-labeled antibody fragments for detection of the recurrence of colorectal carcinoma, J. Nucl. Med., 41:1657-63 (2000).
Yazaki et al., Humanization of the anti-CEA T84.66 antibody based on crystal structure data, Protein Eng. Des. Sel. 17(5):481-9 (2004).
International Search Report issued in connection with PCT/JP2018/025618, dated Sep. 18, 2018.
Kamigaki et al., Improved tumor detection by anti-CEA chimeric Fab oligomers with disulfide linkages in a pancreatic-carcinoma-xenograft model, Int. J. Canc., 66(2):261-267 (1996).
Nittka et al., Radioimmunoimaging of Liver Metastases with PET Using a 64Cu-Labeled CEA Antibody in Transgenic Mice, Plos One, 9(9):e106921 (2014).
Ambrosini et al., 68Ga-DOTA-peptides in the diagnosis of NET, PET Clin., 9 (1): 37-42 (2014).
Lu et al., Linkers Having a Crucial Role in Antibody-Drug Conjugates, Int. J. Mol. Sci.,17(4):561 (2016).
Nakada et al., Novel antibody drug conjugates containing exatecan derivative-based cytotoxic payloads, Bioorg. Med. Chem. Lett., 26(6):1542-1545 (2016).
Russian Patent Application No. 2020141476, Office Action, dated Nov. 25, 2022.
Shire, Formulation of proteins and monoclonal antibodies mAbs, Monoclonal Antibodies: Meeting The Challenges In Manufacturing, Formulation, Delivery And Stability Of Final Drug Product, 93-120: (2015).
Supplementary European Search Report and Opinion, dated Oct. 7, 2022; European Patent Application No. 19870506.3.
Zhu et al., Formulation and protein- and peptide-based parenteral products, In: Parental Medications Third Edition, 222-253: (2010).
Van Brummelen et al., 89Zr-labeled CEA-targeted IL-2 variant immunocytokine in patients with solid tumors: CEA-mediated tumor accumulation and role of IL-2 receptor-binding, Oncotarget, 9(37):24737-24749 (2018).
Singapore Office Action dated Oct. 17, 2022; Singapore Application No. 11202103670X.
Jorgensen, L., et al.. Recent trends in stabilising peptides and proteins in pharmaceutical formulation—considerations in the choice of excipients, Expert Opinion on Drug Delivery, 6(11):1219-1230 (2009).
RU Office Action dated Jan. 13, 2023 for RU Application No. 2021112023.
Wang et al., Antibody Structure, Instability, and Formulation, Journal of Pharmaceutical Sciences, 96(1):1-26 (2007).
Wang, Instability, stabilization, and formulation of liquid protein pharmaceuticals, Int. J. Phann., 185(2):129-88 (1999).

SEQUENCE LISTING

<160> NUMBER OF SEQ ID NOS: 4

<210> SEQ ID NO 1
<211> LENGTH: 678

```
<212> TYPE: DNA
<213> ORGANISM: Artificial Sequence
<220> FEATURE:
<223> OTHER INFORMATION: DNA encoding PB009-01 Fab heavy chain
<220> FEATURE:
<221> NAME/KEY: CDS
<222> LOCATION: (1)..(678)

<400> SEQUENCE: 1 gaa gtg cag ctg gtg gaa tct ggc ggc gga ctg gtg cag cct ggc gga      48
Glu Val Gln Leu Val Glu Ser Gly Gly Gly Leu Val Gln Pro Gly Gly
1               5                   10                  15 tct ctg aga ctg agc tgt gcc gcc agc ggc ttc aac atc cgg gac acc      96
Ser Leu Arg Leu Ser Cys Ala Ala Ser Gly Phe Asn Ile Arg Asp Thr
            20                  25                  30 tac atg cac tgg gtg cgc cag gcc cct ggc aag gga ctg gaa tgg gtg     144
Tyr Met His Trp Val Arg Gln Ala Pro Gly Lys Gly Leu Glu Trp Val
        35                  40                  45 gcc aga atc gac ccc gcc aac ggc aac agc aga tac gtg ccc aag ttc     192
Ala Arg Ile Asp Pro Ala Asn Gly Asn Ser Arg Tyr Val Pro Lys Phe
    50                  55                  60 cag ggc cgg ttc acc atc agc gcc gac acc agc aga aac acc gcc tac     240
Gln Gly Arg Phe Thr Ile Ser Ala Asp Thr Ser Arg Asn Thr Ala Tyr
65                  70                  75                  80 ctg cag atg aac agc ctg cgg gcc gag gac acc gcc gtg tac tac tgt     288
Leu Gln Met Asn Ser Leu Arg Ala Glu Asp Thr Ala Val Tyr Tyr Cys
                85                  90                  95 gcc ccc ttc ggc tac tac gtg tcc gac tac gcc atg gcc tat tgg ggc     336
Ala Pro Phe Gly Tyr Tyr Val Ser Asp Tyr Ala Met Ala Tyr Trp Gly
            100                 105                 110 cag ggc acc ctc gtg aca gtg tcc tca gcc tcc acc aag ggc cca tcg     384
Gln Gly Thr Leu Val Thr Val Ser Ser Ala Ser Thr Lys Gly Pro Ser
        115                 120                 125 gtc ttc ccc ctg gca ccc tcc tcc aag agc acc tct ggg ggc aca gcg     432
Val Phe Pro Leu Ala Pro Ser Ser Lys Ser Thr Ser Gly Gly Thr Ala
    130                 135                 140 gcc ctg ggc tgc ctg gtc aag gac tac ttc ccc gaa ccg gtg acg gtg     480
Ala Leu Gly Cys Leu Val Lys Asp Tyr Phe Pro Glu Pro Val Thr Val
145                 150                 155                 160 tcg tgg aac tca ggc gcc ctg acc agc ggc gtg cac acc ttc ccg gct     528
Ser Trp Asn Ser Gly Ala Leu Thr Ser Gly Val His Thr Phe Pro Ala
                165                 170                 175 gtc cta cag tcc tca gga ctc tac tcc ctt agt agc gtg gtg acc gtg     576
Val Leu Gln Ser Ser Gly Leu Tyr Ser Leu Ser Ser Val Val Thr Val
            180                 185                 190 ccc tcc agc agc ttg ggc acc cag acc tac atc tgc aac gtg aat cac     624
Pro Ser Ser Ser Leu Gly Thr Gln Thr Tyr Ile Cys Asn Val Asn His
        195                 200                 205 aag ccc agc aac acc aag gtg gac aag aaa gtt gag ccc aaa tct tgt     672
Lys Pro Ser Asn Thr Lys Val Asp Lys Lys Val Glu Pro Lys Ser Cys
    210                 215                 220 gac tga                                                              678
Asp
225

<210> SEQ ID NO 2
<211> LENGTH: 225
<212> TYPE: PRT
<213> ORGANISM: Artificial Sequence
<220> FEATURE:
<223> OTHER INFORMATION: Synthetic Construct

<400> SEQUENCE: 2
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Arg Asp Thr
            20                  25                  30

Tyr Met His Trp Val Arg Gln Ala Pro Gly Lys Gly Leu Glu Trp Val
        35                  40                  45

Ala Arg Ile Asp Pro Ala Asn Gly Asn Ser Arg Tyr Val Pro Lys Phe
    50                  55                  60

Gln Gly Arg Phe Thr Ile Ser Ala Asp Thr Ser Arg Asn Thr Ala Tyr
65                  70                  75                  80

Leu Gln Met Asn Ser Leu Arg Ala Glu Asp Thr Ala Val Tyr Tyr Cys
                85                  90                  95

Ala Pro Phe Gly Tyr Tyr Val Ser Asp Tyr Ala Met Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp
225

<210> SEQ ID NO 3
<211> LENGTH: 657
<212> TYPE: DNA
<213> ORGANISM: Artificial Sequence
<220> FEATURE:
<223> OTHER INFORMATION: DNA encoding andibody light chain
<220> FEATURE:
<221> NAME/KEY: CDS
<222> LOCATION: (1)..(657)

<400> SEQUENCE: 3 gac atc cag ctg acc cag agc cct agc agc ctg tct gcc agc gtg ggc      48
Asp Ile Gln Leu Thr Gln Ser Pro Ser Ser Leu Ser Ala Ser Val Gly
1               5                   10                  15 gac aga gtg acc atc acc tgt aga gcc ggc gag agc gtg gac atc ttc      96
Asp Arg Val Thr Ile Thr Cys Arg Ala Gly Glu Ser Val Asp Ile Phe
            20                  25                  30 ggc gtg gga ttt ctg cac tgg tat cag cag aag ccc ggc aag gcc ccc     144
Gly Val Gly Phe Leu His Trp Tyr Gln Gln Lys Pro Gly Lys Ala Pro
        35                  40                  45 aag ctg ctg atc tac aga gcc agc aac ctg gaa agc ggc atc ccc agc     192
Lys Leu Leu Ile Tyr Arg Ala Ser Asn Leu Glu Ser Gly Ile Pro Ser
    50                  55                  60 aga ttc agc ggc agc ggc tcc aga acc gac ttc acc ctg acc atc agc     240
Arg Phe Ser Gly Ser Gly Ser Arg Thr Asp Phe Thr Leu Thr Ile Ser
65                  70                  75                  80
```

| | | | | | | | | | | | | | | | |
|---|---|---|---|---|---|---|---|---|---|---|---|---|---|---|---|
| agc | ctg | cag | ccc | gag | gac | ttc | gcc | acc | tac | tac | tgc | cag | cag | acc | aac | 288
| Ser | Leu | Gln | Pro | Glu | Asp | Phe | Ala | Thr | Tyr | Tyr | Cys | Gln | Gln | Thr | Asn |
| | | | | 85 | | | | | 90 | | | | | 95 | |

| gag | gac | ccc | tac | acc | ttt | ggc | cag | ggc | acc | aag | gtg | gaa | atc | aag | cgt | 336
|---|---|---|---|---|---|---|---|---|---|---|---|---|---|---|---|
| Glu | Asp | Pro | Tyr | Thr | Phe | Gly | Gln | Gly | Thr | Lys | Val | Glu | Ile | Lys | Arg |
| | | | 100 | | | | | 105 | | | | | 110 | | |

| acg | gtg | gct | gca | cca | tct | gtc | ttc | atc | ttc | ccg | cca | tct | gat | gag | cag | 384
|---|---|---|---|---|---|---|---|---|---|---|---|---|---|---|---|
| Thr | Val | Ala | Ala | Pro | Ser | Val | Phe | Ile | Phe | Pro | Pro | Ser | Asp | Glu | Gln |
| | | 115 | | | | | 120 | | | | | 125 | | | |

| ttg | aaa | tct | gga | act | gcc | tct | gtt | gtg | tgc | ctg | ctg | aat | aac | ttc | tat | 432
|---|---|---|---|---|---|---|---|---|---|---|---|---|---|---|---|
| Leu | Lys | Ser | Gly | Thr | Ala | Ser | Val | Val | Cys | Leu | Leu | Asn | Asn | Phe | Tyr |
| | 130 | | | | | 135 | | | | | 140 | | | | |

| ccc | aga | gag | gcc | aaa | gta | cag | tgg | aag | gtg | gat | aac | gcc | ctc | caa | tcg | 480
|---|---|---|---|---|---|---|---|---|---|---|---|---|---|---|---|
| Pro | Arg | Glu | Ala | Lys | Val | Gln | Trp | Lys | Val | Asp | Asn | Ala | Leu | Gln | Ser |
| 145 | | | | | 150 | | | | | 155 | | | | | 160 |

| ggt | aac | tcc | cag | gag | agt | gtc | aca | gag | cag | gac | agc | aag | gac | agc | acc | 528
|---|---|---|---|---|---|---|---|---|---|---|---|---|---|---|---|
| Gly | Asn | Ser | Gln | Glu | Ser | Val | Thr | Glu | Gln | Asp | Ser | Lys | Asp | Ser | Thr |
| | | | | 165 | | | | | 170 | | | | | 175 | |

| tac | agc | ctg | agc | agc | acc | ctg | acg | ctg | agc | aaa | gca | gac | tac | gag | aaa | 576
|---|---|---|---|---|---|---|---|---|---|---|---|---|---|---|---|
| Tyr | Ser | Leu | Ser | Ser | Thr | Leu | Thr | Leu | Ser | Lys | Ala | Asp | Tyr | Glu | Lys |
| | | | 180 | | | | | 185 | | | | | 190 | | |

| cac | aaa | gtc | tac | gcc | tgc | gaa | gtc | acc | cat | cag | ggc | ctg | agc | tcg | ccc | 624
|---|---|---|---|---|---|---|---|---|---|---|---|---|---|---|---|
| His | Lys | Val | Tyr | Ala | Cys | Glu | Val | Thr | His | Gln | Gly | Leu | Ser | Ser | Pro |
| | | 195 | | | | | 200 | | | | | 205 | | | |

| gtc | aca | aag | agc | ttc | aac | agg | gga | gag | tgt | tag | | | | | | 657
|---|---|---|---|---|---|---|---|---|---|---|---|---|---|---|---|
| Val | Thr | Lys | Ser | Phe | Asn | Arg | Gly | Glu | Cys | | | | | | |
| | 210 | | | | | 215 | | | | | | | | | |

<210> SEQ ID NO 4
<211> LENGTH: 218
<212> TYPE: PRT
<213> ORGANISM: Artificial Sequence
<220> FEATURE:
<223> OTHER INFORMATION: Synthetic Construct

<400> SEQUENCE: 4

Asp Ile Gln Leu Thr Gln Ser Pro Ser Ser Leu Ser Ala Ser Val Gly
1               5                   10                  15

Asp Arg Val Thr Ile Thr Cys Arg Ala Gly Glu Ser Val Asp Ile Phe
            20                  25                  30

Gly Val Gly Phe Leu His Trp Tyr Gln Gln Lys Pro Gly Lys Ala Pro
        35                  40                  45

Lys Leu Leu Ile Tyr Arg Ala Ser Asn Leu Glu Ser Gly Ile Pro Ser
    50                  55                  60

Arg Phe Ser Gly Ser Gly Ser Arg Thr Asp Phe Thr Leu Thr Ile Ser
65                  70                  75                  80

Ser Leu Gln Pro Glu Asp Phe Ala Thr Tyr Tyr Cys Gln Gln Thr Asn
                85                  90                  95

Glu Asp Pro Tyr Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

```
                -continued

Tyr Ser Leu Ser Ser Thr Leu Thr Leu Ser Lys Ala Asp Tyr Glu Lys
            180             185             190

His Lys Val Tyr Ala Cys Glu Val Thr His Gln Gly Leu Ser Ser Pro
        195             200             205

Val Thr Lys Ser Phe Asn Arg Gly Glu Cys
    210             215
```

ANTI-HUMAN CEACAM5 ANTIBODY FAB FRAGMENT

CROSS REFERENCE TO RELATED APPLICATIONS

This application is a U.S. national stage of International Application No. PCT/JP2018/025618, filed Jul. 6, 2018, which claims the benefit of Japanese Patent Application No. 2017-133698 filed on Jul. 7, 2017, the entire contents of each of which are fully incorporated herein by reference.

INCORPORATION BY REFERENCE OF MATERIAL SUBMITTED ELECTRONICALLY

A Sequence Listing, which is a part of the present disclosure, is submitted concurrently with the specification as a text file. The name of the text file containing the Sequence Listing is "54845_Seqlisting.txt." The Sequence Listing was created on Jan. 6, 2020, and is 11,312 bytes in size. The subject matter of the Sequence Listing is incorporated herein in its entirety by reference.

TECHNICAL FIELD

The present invention relates to a novel anti-human CEACAM5 antibody Fab fragment. The present invention also relates to a composition for diagnosis comprising the anti-human CEACAM5 antibody Fab fragment, and a method for diagnosing a cancer using the Fab fragment.

BACKGROUND ART

CEA (carcinoembryonic antigen) or CEACAM (carcinoembryonic antigen-related cell adhesion molecule) is a tumor marker discovered in 1965 (J. Exp. Med.; 1965; 121: 439-462; and PNAS; 1969; 64: 161-167), and 23 CEA-related molecules have been revealed so far (BioMed Central Biology; 2010; 8: 12-33). Among them, CEACAM5 is rarely expressed in normal tissues, but is expressed in the fetal gastrointestinal tract or colorectal cancer (BBA; 1990; 1032: 177-189; and Mol. Pathol.; 1999; 52: 174-178). CEACAM5 is known to be also expressed in breast cancer, lung cancer, and thyroid gland cancer (Diagn. Cytopathol.; 1993; 9: 377-382; Cancer Res.; 1990; 50: 6987-6994; Histopathology; 2000; 37: 530-535).

The concentration of CEACAM5 in blood is higher in colorectal cancer patients than in healthy persons (J. Exp. Med.; 1965; 121: 439-462), and CEACAM5 is used as a tumor marker. According to the histological studies of colorectal cancer patients, CEACAM5 is highly expressed in 90% or more tissues (British J. Cancer; 2013; 108: 662-667).

Since the early metastasis of colorectal cancer is localized to the liver, early detection and treatment of hepatic metastasis can reduce recurrence rates (Cell Mol. Gastroenterol. Hepatol.; 2017; 3: 163-173). The diagnosis of hepatic metastasis employs CT (computer tomography), MRI (magnetic resonance imaging), or FDG-PET (fluorodeoxyglucose-positron emission tomography). The detection sensitivity of CT, MRI, and FDG-PET is 74.4, 80.3, and 81.4%, respectively, and detection sensitivity to 1 cm or smaller tumor is reduced to 47.3% for CT and 60.2% for MRI (Radiology; 2010; 257: 674-684). MRI using liver-specific contrast media is also employed, though its detection sensitivity to 1 cm or smaller tumor is 29 to 38% (Radiology; 2005; 237: 89-98).

Anticancer agents or antibodies labeled with a metal radioisotope are used for diagnosing or treating cancers. Targeting using antibodies has high specificity for tumor cells and causes fewer adverse events. Some monoclonal antibodies labeled with a metal radioisotope have been clinically applied to diagnosis and treatment so far (Cancer Control; 2012; 19: 196-203).

Meanwhile, antibodies generally have a long half-life in blood and require a period as long as 4 days to 5 days for reaching a tumor-to-blood ratio that confers a signal-to-background ratio sufficient for visualizing a cancer, after administration into the body (Clin. Pharmacol. Ther.; 2010; 87: 586-592). Also, the Fc regions of antibodies cause a pharmacological effect of antibody-dependent cellular cytotoxicity (ADCC) or complement-dependent cytotoxicity (CDC) (Glycoconj. J.; 2013; 30: 227-236; and Curr. Opin. Biotechnol.; 2002; 13: 609-614). Furthermore, antibodies are metabolized in the liver and therefor highly accumulate in the liver, regardless of a target. However, it is difficult to detect lesions of hepatic metastasis using antibodies because the early metastasis of colorectal cancer is localized to the liver (Clin. Pharmacol. Ther.; 2010; 87: 586-592).

Low-molecular recombinant antibody fragments such as Fab, scFv, and diabody easily arrive at lesions because of their high tissue penetration and are utilized as therapeutic antibodies because production at low cost using an expression system in E. coli or yeasts can be expected. On the other hand, their utilization as a diagnostic drug has also been reported because of their short half-lives in blood and the feature of renal excretion (Nat. Biotechnol.; 2005; 23: 1126-1136).

A M5A (PTL 1), a humanized antibody of mouse monoclonal antibody T84.66, is known as an anti-human CEACAM5 antibody applied to a diagnostic drug. It has been reported that M5A labeled with $^{64}$Cu requires a lapse of 22 hours or longer after administration for obtaining favorable PET images in a test using subcutaneously cancer cell-transplanted mice (NPL 1), and is taken up into a normal tissue of the liver and a lesion site of the liver at the same level 3 hours after administration and with significant difference after a lapse of 24 hours in a test using mouse models with hepatic metastasis (NPL 2).

As for a fragment of an anti-human CEACAM5 antibody, it has been reported that CEA-Scan, $^{99m}$Tc-labeled Fab' of mouse monoclonal antibody NP-4, can be utilized in the diagnosis of colorectal cancer (NPL 3). However, the uptake of CEA-Scan into a lesion site does not exceed its uptake into the normal liver, and its detection sensitivity for hepatic metastasis is lower than that of FDG-PET (NPL 4). CEA-Scan was approved as a diagnostic drug for colorectal cancer by FDA in 1999, but is no longer sold (NPL 5).

CITATION LIST

Patent Literature

PTL 1: International Publication No. WO 2005/086875

Non Patent Literature

NPL 1: Bioconjug. Chem.; 2008; 19: 89-96
NPL 2: PLOS ONE; 2014; 9 (9): e106921
NPL 3: Ann. Surg.; 1997; 226: 621-631
NPL 4: J. Nucl. Med.; 2000; 41: 1657-1663
NPL 5: Kenneth T. Cheng, "99mTc-Arcitumomab", [online], Update: Mar. 17, 2008, Molecular Imaging and Contrast Agent Database, [searched on May 17, 2017], internet <URL: www.ncbi.nlm.nih.gov/books/NBK23676/

SUMMARY OF INVENTION

Technical Problem

Monovalent Fab fragments have a molecular weight of approximately 50 kDa, which is smaller than that (approximately 150 kDa) of antibodies, undergo renal excretion, and also have a short half-life in blood. Hence, they reach a tumor-to-blood ratio that confers a signal-to-background ratio sufficient for being able to detect hepatic metastasis and visualizing a cancer within 2 to 32 hours after administration. They lack a Fc region and therefore cause neither ADCC nor CDC. From these features, the Fab fragments can be expected to be more effective as diagnostic drugs as compared with antibodies.

However, the binding activity of the Fab fragments is often attenuated because of being a small molecule. Antibodies must be labeled with a detectable substance such as a PET tracer or a fluorescent dye for their utilization as in vivo diagnostic drugs. A further problem of the Fab fragments is the attenuation of their binding activity due to labeling with a substance.

An object of the present invention is to provide an anti-human CEACAM5 antibody Fab fragment that is useful for detecting human CEACAM5 and is expected to accumulate in a cancer lesion within a short time (e.g., 4 hours) after administration. Another object of the present invention is to provide a composition for diagnosis comprising the Fab fragment that is expected to permit diagnosis on the day of administration, and a diagnosis method using the same.

Solution to Problem

The present inventors have conducted considerable diligent studies on the preparation of an anti-human CEACAM5 antibody Fab fragment useful for detecting human CEACAM5, and consequently prepared an anti-human CEACAM5 antibody Fab fragment comprising a heavy chain variable region consisting of an amino acid sequence from amino acid positions 1 to 121 of SEQ ID NO: 2, and a light chain variable region consisting of an amino acid sequence from amino acid positions 1 to 112 of SEQ ID NO: 4 (Example 1) and found that: the anti-human CEACAM5 antibody Fab fragment is free from the attenuation of the binding activity against human CEACAM5 by the binding of a labeling moiety (Example 3); and a conjugate comprising the anti-human CEACAM5 antibody Fab fragment accumulates in human CEACAM5-positive cancer cells in subcutaneous transplantation models and liver transplantation models 4 hours after administration and permits detection of the human CEACAM5-positive cancer cells (Examples 5 and 6). Specifically, the present invention provides an anti-human CEACAM5 antibody Fab fragment that accumulates in a cancer, and a conjugate comprising the anti-human CEACAM5 antibody Fab fragment.

The present invention includes aspects given below as medically or industrially useful substances and methods.

Specifically, in one aspect, the present invention can be as follows:

(1) An anti-human CEACAM5 antibody Fab fragment comprising a heavy chain fragment comprising a heavy chain variable region comprising CDR1 consisting of an amino acid sequence from amino acid positions 31 to 35 of SEQ ID NO: 2, CDR2 consisting of an amino acid sequence from amino acid positions 50 to 66 of SEQ ID NO: 2, and CDR3 consisting of an amino acid sequence from amino acid positions 99 to 110 of SEQ ID NO: 2, and a light chain comprising a light chain variable region comprising CDR1 consisting of an amino acid sequence from amino acid positions 24 to 38 of SEQ ID NO: 4, CDR2 consisting of an amino acid sequence from amino acid positions 54 to 60 of SEQ ID NO: 4, and CDR3 consisting of an amino acid sequence from amino acid positions 93 to 101 of SEQ ID NO: 4.

(2) The anti-human CEACAM5 antibody Fab fragment according to (1) selected from the group consisting of the following (a) and (b):

(a) an anti-human CEACAM5 antibody Fab fragment comprising a heavy chain fragment comprising a heavy chain variable region consisting of an amino acid sequence from amino acid positions 1 to 121 of SEQ ID NO: 2 and a light chain comprising a light chain variable region consisting of an amino acid sequence from amino acid positions 1 to 112 of SEQ ID NO: 4; and (b) an anti-human CEACAM5 antibody Fab fragment comprising a heavy chain fragment comprising a heavy chain variable region derived from a heavy chain variable region consisting of an amino acid sequence from amino acid positions 1 to 121 of SEQ ID NO: 2 by the modification of glutamic acid at amino acid position 1 of SEQ ID NO: 2 into pyroglutamic acid, and a light chain comprising a light chain variable region consisting of an amino acid sequence from amino acid positions 1 to 112 of SEQ ID NO: 4.

(3) The anti-human CEACAM5 antibody Fab fragment according to (2) selected from the group consisting of the following (a) and (b):

(a) an anti-human CEACAM5 antibody Fab fragment comprising a heavy chain fragment consisting of the amino acid sequence represented by SEQ ID NO: 2 and a light chain consisting of the amino acid sequence represented by SEQ ID NO: 4; and (b) an anti-human CEACAM5 antibody Fab fragment comprising a heavy chain fragment derived from a heavy chain fragment consisting of the amino acid sequence represented by SEQ ID NO: 2 by the modification of glutamic acid at amino acid position 1 of SEQ ID NO: 2 into pyroglutamic acid, and a light chain consisting of the amino acid sequence represented by SEQ ID NO: 4.

(4) The anti-human CEACAM5 antibody Fab fragment according to (3), comprising a heavy chain fragment consisting of the amino acid sequence represented by SEQ ID NO: 2 and a light chain consisting of the amino acid sequence represented by SEQ ID NO: 4.

(5) A conjugate comprising a labeling moiety and an anti-human CEACAM5 antibody Fab fragment according to any of (1) to (4).

(6) The conjugate according to (5), wherein the labeling moiety is (i) a ligand and a linker, (ii) a ligand, (iii) a fluorescent dye and a linker, or (iv) a fluorescent dye.

(7) The conjugate according to (6), wherein the labeling moiety is (i) a ligand and a linker, or (ii) a ligand.

(8) The conjugate according to (7), wherein the ligand is a ligand represented by the following formula (A):

[Chemical Formula 1]

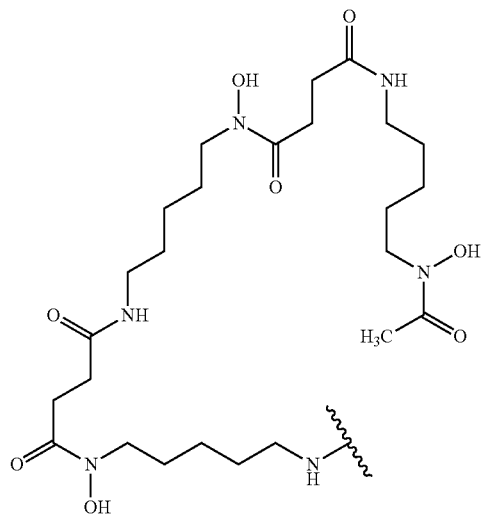

(A)

wherein the wavy line represents binding to the anti-human CEACAM5 antibody Fab fragment or the linker.

(9) The conjugate according to (7), wherein the labeling moiety is (i) a ligand and a linker, wherein the ligand and the linker are a group represented by the following formula (A'):

[Chemical Formula 2]

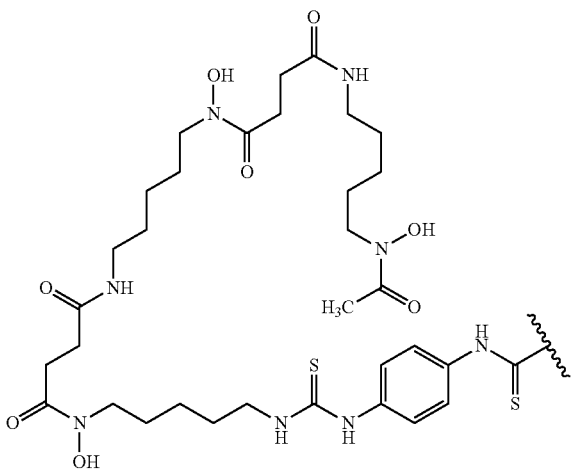

(A')

wherein the wavy line represents binding to the anti-human CEACAM5 antibody Fab fragment.

(10) The conjugate according to (9), wherein the anti-human CEACAM5 antibody Fab fragment is bound to the carbon atom of a labeling moiety terminal C(=S) group via an amino group in the Fab fragment.

(11) The conjugate according to (7) represented by the following formula (I):

$(L-X)_p$-Ab  (I)

wherein Ab is the anti-human CEACAM5 antibody Fab fragment;
L is the ligand;
X is the linker or a bond; and
p is a natural number of 1 to 25.

(12) The conjugate according to (11), wherein L is a ligand represented by the following formula (A):

[Chemical Formula 3]

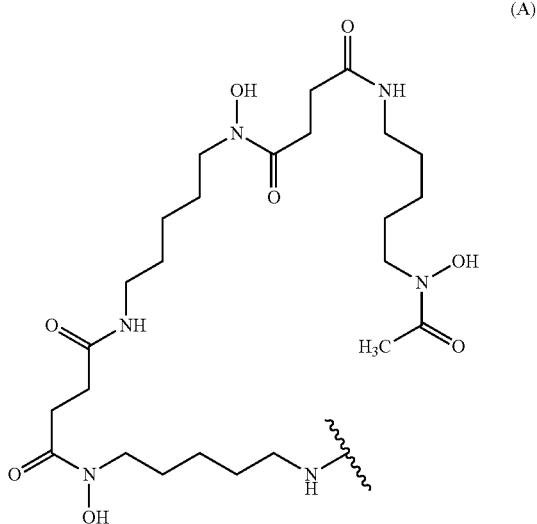

(A)

wherein the wavy line represents binding to X (or Ab when X is a bond).

(13) The conjugate according to (9) or (12) represented by the following formula (II):

[Chemical Formula 4]

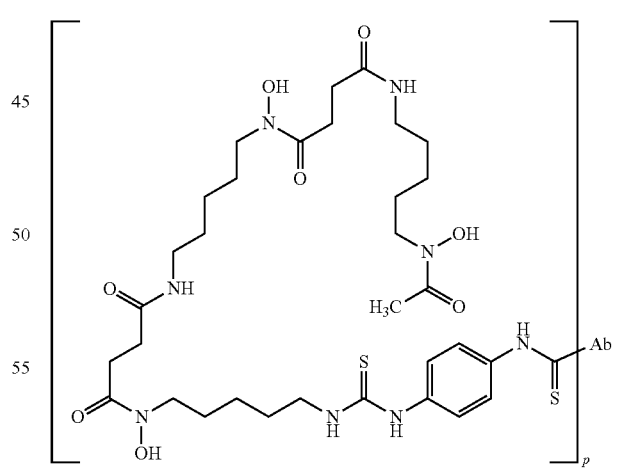

(II)

wherein Ab is the anti-human CEACAM5 antibody Fab fragment; and
p is a natural number of 1 to 25, wherein
Ab is bound to the carbon atom of labeling moiety terminal C(=S) via an amino group in the Ab.

(14) The conjugate according to any of (11) to (13), wherein p is a natural number of 1 to 16.

(15) The conjugate according to any of (11) to (13), wherein p is a natural number of 4 to 16.
(16) The conjugate according to any of (6) to (15), further comprising a metal.
(17) The conjugate according to (16), wherein the metal is a metal radioisotope.
(18) The conjugate according to (16), wherein the metal is $^{89}$Zr.
(19) The conjugate according to (17) or (18) for use as a PET tracer.
(20) A polynucleotide selected from the group consisting of the following (a) and (b):
(a) a polynucleotide comprising a nucleotide sequence encoding the heavy chain fragment of anti-human CEACAM5 antibody Fab fragment (a) according to (2); and
(b) a polynucleotide comprising a nucleotide sequence encoding the light chain of anti-human CEACAM5 antibody Fab fragment (a) according to (2).
(21) A polynucleotide selected from the group consisting of the following (a) and (b):
(a) a polynucleotide comprising a nucleotide sequence encoding the heavy chain fragment of an anti-human CEACAM5 antibody Fab fragment according to (4); and
(b) a polynucleotide comprising a nucleotide sequence encoding the light chain of the anti-human CEACAM5 antibody Fab fragment according to (4).
(22) An expression vector comprising the following (a) and/or (b):
(a) a polynucleotide comprising a nucleotide sequence encoding the heavy chain fragment of anti-human CEACAM5 antibody Fab fragment (a) according to (2); and
(b) a polynucleotide comprising a nucleotide sequence encoding the light chain of anti-human CEACAM5 antibody Fab fragment (a) according to (2).
(23) An expression vector comprising the following (a) and/or (b):
(a) a polynucleotide comprising a nucleotide sequence encoding the heavy chain fragment of an anti-human CEACAM5 antibody Fab fragment according to (4); and
(b) a polynucleotide comprising a nucleotide sequence encoding the light chain of the anti-human CEACAM5 antibody Fab fragment according to (4).
(24) A host cell selected from the group consisting of the following (a) to (d):
(a) a host cell transformed with an expression vector comprising a polynucleotide comprising a nucleotide sequence encoding the heavy chain fragment of anti-human CEACAM5 antibody Fab fragment (a) according to (2);
(b) a host cell transformed with an expression vector comprising a polynucleotide comprising a nucleotide sequence encoding the light chain of anti-human CEACAM5 antibody Fab fragment (a) according to (2);
(c) a host cell transformed with an expression vector comprising a polynucleotide comprising a nucleotide sequence encoding the heavy chain fragment of anti-human CEACAM5 antibody Fab fragment (a) according to (2) and a polynucleotide comprising a nucleotide sequence encoding the light chain of anti-human CEACAM5 antibody Fab fragment (a) according to (2); and
(d) a host cell transformed with an expression vector comprising a polynucleotide comprising a nucleotide sequence encoding the heavy chain fragment of anti-human CEACAM5 antibody Fab fragment (a) according to (2) and an expression vector comprising a polynucleotide comprising a nucleotide sequence encoding the light chain of anti-human CEACAM5 antibody Fab fragment (a) according to (2).
(25) A host cell selected from the group consisting of the following (a) to (d):
(a) a host cell transformed with an expression vector comprising a polynucleotide comprising a nucleotide sequence encoding the heavy chain fragment of an anti-human CEACAM5 antibody Fab fragment according to (4);
(b) a host cell transformed with an expression vector comprising a polynucleotide comprising a nucleotide sequence encoding the light chain of the anti-human CEACAM5 antibody Fab fragment according to (4);
(c) a host cell transformed with an expression vector comprising a polynucleotide comprising a nucleotide sequence encoding the heavy chain fragment of the anti-human CEACAM5 antibody Fab fragment according to (4) and a polynucleotide comprising a nucleotide sequence encoding the light chain of the anti-human CEACAM5 antibody Fab fragment according to (4); and
(d) a host cell transformed with an expression vector comprising a polynucleotide comprising a nucleotide sequence encoding the heavy chain fragment of the anti-human CEACAM5 antibody Fab fragment according to (4) and an expression vector comprising a polynucleotide comprising a nucleotide sequence encoding the light chain of the anti-human CEACAM5 antibody Fab fragment according to (4).
(26) A method for producing an anti-human CEACAM5 antibody Fab fragment, comprising the step of culturing a host cell selected from the group consisting of the following (a) to (c) to express the anti-human CEACAM5 antibody Fab fragment:
(a) a host cell transformed with an expression vector comprising a polynucleotide comprising a nucleotide sequence encoding the heavy chain fragment of anti-human CEACAM5 antibody Fab fragment (a) according to (2) and a polynucleotide comprising a nucleotide sequence encoding the light chain of anti-human CEACAM5 antibody Fab fragment (a) according to (2);
(b) a host cell transformed with an expression vector comprising a polynucleotide comprising a nucleotide sequence encoding the heavy chain fragment of anti-human CEACAM5 antibody Fab fragment (a) according to (2) and an expression vector comprising a polynucleotide comprising a nucleotide sequence encoding the light chain of anti-human CEACAM5 antibody Fab fragment (a) according to (2); and
(c) a host cell transformed with an expression vector comprising a polynucleotide comprising a nucleotide sequence encoding the heavy chain fragment of anti-human CEACAM5 antibody Fab fragment (a) according to (2), and a host cell transformed with an expression vector comprising a polynucleotide comprising a nucleotide sequence encoding the light chain of anti-human CEACAM5 antibody Fab fragment (a) according to (2).
(27) A method for producing an anti-human CEACAM5 antibody Fab fragment, comprising the step of culturing a host cell selected from the group consisting of the following (a) to (c) to express the anti-human CEACAM5 antibody Fab fragment:
(a) a host cell transformed with an expression vector comprising a polynucleotide comprising a nucleotide sequence encoding the heavy chain fragment of an anti-human CEACAM5 antibody Fab fragment according to (4) and a polynucleotide comprising a nucleotide sequence encoding the light chain of the anti-human CEACAM5 antibody Fab fragment according to (4);
(b) a host cell transformed with an expression vector comprising a polynucleotide comprising a nucleotide sequence encoding the heavy chain fragment of the anti-human CEACAM5 antibody Fab fragment according to (4) and an expression vector comprising a polynucleotide comprising a nucleotide sequence encoding the light chain of the anti-human CEACAM5 antibody Fab fragment according to (4); and (c) a host cell transformed with an expression vector comprising a polynucleotide comprising a nucleotide sequence encoding the heavy chain fragment of the anti-human CEACAM5 antibody Fab fragment according to (4), and a host cell transformed with an expression vector comprising a polynucleotide comprising a nucleotide sequence encoding the light chain of the anti-human CEACAM5 antibody Fab fragment according to (4).

(28) A method for producing a conjugate comprising a labeling moiety and an anti-human CEACAM5 antibody Fab fragment, comprising the steps of: preparing the anti-human CEACAM5 antibody Fab fragment by a method according to (26) or (27); and covalently binding the Fab fragment to the labeling moiety.

(29) A method for producing a conjugate comprising a ligand and an anti-human CEACAM5 antibody Fab fragment, comprising the steps of: preparing the anti-human CEACAM5 antibody Fab fragment by a method according to (26) or (27); and covalently binding the Fab fragment to the ligand via a linker or directly.

(30) A method for producing a conjugate comprising a labeling moiety labeled with a metal radioisotope and an anti-human CEACAM5 antibody Fab fragment, comprising the steps of: producing a conjugate comprising a ligand and an anti-human CEACAM5 antibody Fab fragment by a method according to (29); and binding the metal radioisotope to the ligand of the conjugate through a coordinate bond.

(31) A composition for diagnosis comprising a conjugate according to any of (16) to (19), and a pharmaceutically acceptable carrier.

(32) The composition for diagnosis according to (31) which is a clinical staging drug.

(33) The composition for diagnosis according to (31) or (32) for use in the diagnosis of colorectal cancer, breast cancer, lung cancer, thyroid gland cancer or a cancer resulting from the metastasis thereof.

(34) The composition for diagnosis according to (33) for use in the diagnosis of colorectal cancer or a cancer resulting from the metastasis of colorectal cancer.

(35) The composition for diagnosis according to (34), wherein the cancer resulting from the metastasis of colorectal cancer is metastatic liver cancer.

(36) Use of a conjugate according to any of (16) to (19) for the production of a composition for diagnosis of colorectal cancer, breast cancer, lung cancer, thyroid gland cancer or a cancer resulting from the metastasis thereof.

(37) The conjugate according to any of (16) to (19) for use in the diagnosis of colorectal cancer, breast cancer, lung cancer, thyroid gland cancer or a cancer resulting from the metastasis thereof.

(38) A method for diagnosing colorectal cancer, breast cancer, lung cancer, thyroid gland cancer or a cancer resulting from the metastasis thereof, comprising administering a conjugate according to any of (16) to (19) to a subject.

(39) The anti-human CEACAM5 antibody Fab fragment according to any of (1) to (4) for use as a conjugate comprising a labeling moiety.

(40) Use of an anti-human CEACAM5 antibody Fab fragment according to any of (1) to (4) for the production of a conjugate comprising a labeling moiety.

(41) The anti-human CEACAM5 antibody Fab fragment according to (39), wherein the conjugate comprising a labeling moiety is a conjugate according to any of (5) to (18).

(42) The use of an anti-human CEACAM5 antibody Fab fragment according to (40), wherein the conjugate comprising a labeling moiety is a conjugate according to any of (5) to (18).

Advantageous Effects of Invention

The anti-human CEACAM5 antibody Fab fragment of the present invention is useful for detecting human CEACAM5 and is expected to be useful in the diagnosis of a cancer such as colorectal cancer, breast cancer, lung cancer, thyroid gland cancer or a cancer resulting from the metastasis thereof.

DESCRIPTION OF EMBODIMENTS

Figure 1A:
FIG. 1A is a representative image taken by PET 4 hours after administration of PB009-03 to a mouse in which human colorectal cancer cell line LS174T cells (human CEACAM5-positive cells) were subcutaneously transplanted to the right shoulder while human colorectal cancer cell line HCT-15 cells (human CEACAM5-negative cells) were subcutaneously transplanted to the left shoulder. Since the mouse was photographed face-down, the right circle depicts the LS174T cell-transplanted right shoulder of the mouse, and the left circle depicts the HCT-15 cell-transplanted left shoulder of the mouse. The right bar depicts a maximum standardized uptake value (SUV-Max) to tumor.

Hereinafter, the present invention will be described in detail. However, the present invention is not limited thereby. Scientific terms and technical terms used in relation to the present invention have meanings generally understood by those skilled in the art, unless otherwise specified herein.

The present inventors have conducted considerable diligent studies on the preparation of an anti-human CEACAM5 antibody or an antigen binding fragment thereof and consequently successfully prepared an anti-human CEACAM5 antibody Fab fragment useful for detecting human CEACAM5.

The basic structure of an antibody molecule is common among classes and is constituted by heavy chains having a molecular weight of 50000 to 70000 and light chains having a molecular weight of 20000 to 30000. The heavy chain usually consists of a polypeptide chain comprising approximately 440 amino acids, has a structure characteristic of each class, and is called γ, μ, α, δ, and ε chains corresponding to IgG, IgM, IgA, IgD, and IgE. IgG further has IgG1, IgG2, IgG3, and IgG4 which are called γ1, γ2, γ3, and γ4, respectively. The light chain usually consists of a polypeptide chain comprising approximately 220 amino acids and is known as two types, L and K types, which are called λ and κ chains, respectively. As for the peptide configuration of the basic structure of the antibody molecule, two homologous heavy chains and two homologous light chains are linked through disulfide bonds (S—S bonds) and non-covalent bonds to form a molecular weight of 150000 to 190000. The two light chains can pair with any of the heavy chains. An individual antibody molecule is constantly made up of two identical light chains and two identical heavy chains.

Four (or five for μ and ε chains) and two intrachain S—S bonds are present in the heavy chain and the light chain, respectively, and each constitute one loop per 100 to 110 amino acid residues. This conformation is similar among the loops and is called structural unit or domain. For both the heavy chain and the light chain, a domain positioned on the N-terminal side does not have a constant amino acid sequence even among preparations from the same classes (subclasses) of animals of the same species, and is thus called variable region. The respective domains are called heavy chain variable region ($V_H$ domain) and light chain variable region ($V_L$ domain). An amino acid sequence on the C-terminal side therefrom is almost constant on a class or subclass basis and called constant region. The respective domains are represented by $C_{H1}$, $C_{H2}$, $C_{H3}$ and $C_L$.

The binding specificity of the antibody for an antigen depends on the amino acid sequence of a moiety constituted by the heavy chain variable region and the light chain variable region. On the other hand, biological activity such as binding to complements or various cells reflects the difference in structure among the constant regions of Igs of respective classes. It is known that the variability of the heavy chain and light chain variable regions is limited substantially by three small hypervariable regions present in both the chains. These regions are called complementarity determining regions (CDRs; CDR1, CDR2, and CDR3 in order from the N-terminal side). The remaining moieties of the variable region are called framework regions (FRs) and are relatively constant.

A region between the $C_{H1}$ domain and the $C_{H2}$ domain of the heavy chain constant region of an antibody is called hinge region. This region is rich in proline residues and contains a plurality of interchain S—S bonds that connect two heavy chains. For example, the hinge regions of human IgG1, IgG2, IgG3, and IgG4 contain 2, 4, 11, and 2 cysteine residues, respectively, which constitute S—S bonds between the heavy chains. The hinge region is a region highly sensitive to a proteolytic enzyme such as papain or pepsin. In the case of digesting an antibody with papain, the heavy chains are cleaved at a position on the N-terminal side from the inter-heavy chain S—S bonds of the hinge region and thus decomposed into two Fab fragments and one Fc fragment. The Fab fragment is constituted by a light chain and a heavy chain fragment comprising a heavy chain variable region, a Cm domain and a portion of the hinge region. The Fab fragment comprises variable regions and has antigen binding activity.

<Anti-Human CEACAM5 Antibody Fab Fragment of Present Invention>

The anti-human CEACAM5 antibody Fab fragment of the present invention includes a Fab fragment having the following feature:

an anti-human CEACAM5 antibody Fab fragment comprising a heavy chain fragment comprising a heavy chain variable region consisting of an amino acid sequence from amino acid positions 1 to 121 of SEQ ID NO: 2 and a light chain comprising a light chain variable region consisting of an amino acid sequence from amino acid positions 1 to 112 of SEQ ID NO: 4.

Any constant region of Igγ1, Igγ2, Igγ3 or Igγ4, etc. can be selectable as the heavy chain constant region of the anti-human CEACAM5 antibody Fab fragment of the present invention. In one embodiment, the heavy chain constant region of the anti-human CEACAM5 antibody Fab fragment of the present invention is a human Igγ1 constant region.

Any constant region of Igλ or Igκ can be selectable as the light chain constant region of the anti-human CEACAM5 antibody Fab fragment of the present invention. In one embodiment, the light chain constant region of the anti-human CEACAM5 antibody Fab fragment of the present invention is a human Igκ constant region.

In one embodiment, the anti-human CEACAM5 antibody Fab fragment of the present invention is the following Fab fragment:

an anti-human CEACAM5 antibody Fab fragment comprising a heavy chain fragment consisting of the amino acid sequence represented by SEQ ID NO: 2 and a light chain consisting of the amino acid sequence represented by SEQ ID NO: 4.

In the case of expressing an antibody including a Fab fragment in cells, the antibody is known to undergo a posttranslational modification. Examples of the posttranslational modification include the cleavage of heavy chain C-terminal lysine by carboxypeptidase, the modification of heavy chain and light chain N-terminal glutamine or glutamic acid into pyroglutamic acid by pyroglutamylation, glycosylation, oxidation, deamidation, and glycation. Such a posttranslational modification is known to occur in various antibodies (J. Pharm. Sci., 2008; 97: 2426-2447).

The anti-human CEACAM5 antibody Fab fragment of the present invention can also include a Fab fragment resulting from the posttranslational modification. Examples of the anti-human CEACAM5 antibody Fab fragment of the present invention that can result from the posttranslational modification include an anti-human CEACAM5 antibody Fab fragment having an N-terminally pyroglutamylated heavy chain. It is known in the art that such a posttranslational modification by N-terminal pyroglutamylation has no marked influence on the activity of the antibody (Anal. Biochem., 2006; 348: 24-39).

In one embodiment, the anti-human CEACAM5 antibody Fab fragment of the present invention is an anti-human CEACAM5 antibody Fab fragment having the following feature: an anti-human CEACAM5 antibody Fab fragment comprising a heavy chain fragment comprising a heavy chain variable region derived from a heavy chain variable region consisting of an amino acid sequence from amino acid positions 1 to 121 of SEQ ID NO: 2 by the modification of glutamic acid at amino acid position 1 of SEQ ID NO: 2 into pyroglutamic acid, and a light chain comprising a light chain variable region consisting of an amino acid sequence from amino acid positions 1 to 112 of SEQ ID NO: 4.

In another embodiment, the anti-human CEACAM5 antibody Fab fragment of the present invention is an anti-human CEACAM5 antibody Fab fragment having the following feature:
an anti-human CEACAM5 antibody Fab fragment comprising a heavy chain fragment derived from a heavy chain fragment consisting of the amino acid sequence represented by SEQ ID NO: 2 by the modification of glutamic acid at amino acid position 1 of SEQ ID NO: 2 into pyroglutamic acid, and a light chain consisting of the amino acid sequence represented by SEQ ID NO: 4.

The present invention also includes an anti-human CEACAM5 antibody Fab fragment having the following feature:
an anti-human CEACAM5 antibody Fab fragment comprising a heavy chain fragment comprising a heavy chain variable region comprising CDR1 consisting of an amino acid sequence from amino acid positions 31 to 35 of SEQ ID NO: 2, CDR2 consisting of an amino acid sequence from amino acid positions 50 to 66 of SEQ ID NO: 2, and CDR3 consisting of an amino acid sequence from amino acid positions 99 to 110 of SEQ ID NO: 2, and a light chain comprising a light chain variable region comprising CDR1 consisting of an amino acid sequence from amino acid positions 24 to 38 of SEQ ID NO: 4, CDR2 consisting of an amino acid sequence from amino acid positions 54 to 60 of SEQ ID NO: 4, and CDR3 consisting of an amino acid sequence from amino acid positions 93 to 101 of SEQ ID NO: 4.

The anti-human CEACAM5 antibody Fab fragment of the present invention binds to human CEACAM5. A method for measuring the binding activity of the obtained anti-human CEACAM5 antibody Fab fragment against human CEACAM5 includes methods such as analysis by surface plasmon resonance (SPR) and ELISA. In the case of using, for example, analysis by SPR, an association rate constant (ka), a dissociation rate constant (kd), and a dissociation constant ($K_D$) can be measured by using Biacore T200 (GE Healthcare Japan Corp.), immobilizing Biotin CAPture Kit (GE Healthcare Japan Corp.) and biotinylated human CEACAM5 onto a sensor chip, and adding a serially diluted Fab fragment thereto.

The anti-human CEACAM5 antibody Fab fragment of the present invention can be readily prepared by those skilled in the art using a method known in the art on the basis of sequence information on the heavy chain fragment and the light chain of the anti-human CEACAM5 antibody Fab fragment of the present invention disclosed herein. The anti-human CEACAM5 antibody Fab fragment of the present invention can be produced according to, but not particularly limited to, a method described in, for example, <Method for producing anti-human CEACAM5 antibody Fab fragment of present invention> mentioned later.

<Conjugate of Present Invention>

The conjugate of the present invention is a conjugate comprising a labeling moiety and the anti-human CEACAM5 antibody Fab fragment of the present invention.

The "labeling moiety" is (i) a ligand and a linker, (ii) a ligand, (iii) a fluorescent dye and a linker, or (iv) a fluorescent dye. A certain form is (i) a ligand and a linker, or (ii) a ligand comprising a metal. A certain form is (iii) a fluorescent dye and a linker. A certain form is (i) a ligand and a linker. The ligand of the "labeling moiety" may further comprise a metal. A certain form is (i) a ligand and a linker comprising a metal or (ii) a ligand comprising it, and another form is (i) a ligand forming a chelate complex with a metal, and a linker, or (ii) a ligand forming a chelate complex with a metal.

The conjugate of the present invention comprising a metal, a fluorescent dye or a non-metal radioisotope can be used in various contrast media and the like and is used in, for example, an MRI contrast medium, a PET tracer, and a fluorescently labeled molecular imaging agent.

In the present specification, the "metal" means a paramagnetic metal ion or a metal radioisotope. The metal is not particularly limited as long as the metal forms a coordinate bond with each ligand. An appropriate known combination of a ligand and the metal is selected according to the usage purpose of the conjugate.

The paramagnetic metal ion is suitably used in an MRI contrast medium. Examples of the form of the paramagnetic metal ion include, but are not limited to, $Fe^{2+}$, $Fe^{3+}$, $Cu^{2+}$, $Ni^{2+}$, $Rh^{2+}$, $Co^{2+}$, $Gd^{3+}$, $Eu^{3+}$, $Dy^{3+}$, $Tb^{3+}$, $Pm^{3+}$, $Nd^{3+}$, $Tm^{3+}$, $Ce^{3+}$, $Y^{3+}$, $Ho^{3+}$, $Er^{3+}$, $La^{3+}$, $Yb^{3+}$, $Mn^{3+}$, and $Mn^{2+}$. A certain form is $Gd^{3+}$, $Mn^{3+}$, $Mn^{2+}$, $Fe^{2+}$, or $Fe^{3+}$. A certain form is $Mn^{3+}$ or $Mn^{2+}$. In this case, halogen or the like can be used as a counter anion in the conjugate. Alternatively, the counter anion may be $C(=O)O^-$ of the ligand. The conjugate may further have a counter cation such as $Na^+$.

The metal radioisotope is used in, for example, a PET tracer. Examples of the form of the metal radioisotope include, but are not limited to, $^{89}Zr$, $^{51}Mn$, $^{52}Fe$, $^{60}Cu$, $^{67}Ga$, $^{68}Ga$, $^{72}As$, $^{99m}Tc$, and $^{111}In$. A certain form is $^{89}Zr$, $^{60}Cu$, $^{67}Ga$, $^{68}Ga$, $^{99m}Tc$, or $^{111}In$. A certain form is a radioisotope of zirconium. A certain form is $^{89}Zr$.

The "ligand" is a moiety capable of forming a chelate complex with a metal in this conjugate and means a group constituted by a chelating agent in a certain form. The constituted group is a group having a bond by the removal of a proton from the chelating agent.

The "chelating agent" is a compound that can form a coordinate bond with a metal.

Examples of the "chelating agent" include siderophore and non-siderophore. Examples of a certain form include MAG3 (mercaptoacetyl-glycyl-glycyl-glycine, CAS No: 66516-09-4) and known reactive derivatives thereof. Examples of the siderophore include hydroxamic acid type, catechol type, and mixed ligand type. Examples of the hydroxamic acid-type siderophore include ferrichrome, deferoxamine (DFO) represented by the following formula:

[Chemical Formula 5]

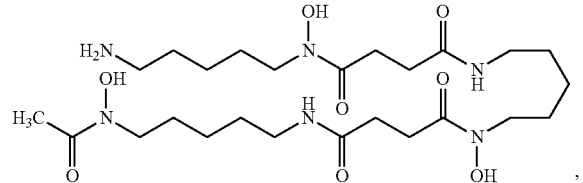

fusarinine C, ornibactin, rhodotorulic acid, and known reactive derivatives thereof. Examples of the catechol-type siderophore include enterobactin, bacillibactin, vibriobactin, and known reactive derivatives thereof. Examples of the mixed ligand-type siderophore include azotobactin, pyoverdine, yersiniabactin, and known reactive derivatives thereof. In the case of the siderophore, DFO can be reacted via its reactive functional group —$NH_2$ with the linker or the Fab fragment, and the siderophore other than DFO can also be reacted via its reactive functional group such as a carboxy group, a hydroxy group, or an amino group with the linker or the Fab fragment by a method usually used by those skilled in the art.

Examples of the non-siderophore include DTPA (diethylenetriaminepentaacetic acid, CAS No: 67-43-6), DTPA-BMA (1,7-bis(methylcarbamoylmethyl)-1,4,7-triazaheptane-1,4,7-triacetic acid, CAS No: 119895-95-3), EOB-DTPA (ethoxybenzyl-DTPA, 2-[[(2S)-2-[bis(carboxymethyl)amino]-3-(4-ethoxyphenyl)propyl]-[2-[bis(carboxymethyl)amino]ethyl]amino]acetic acid), TTHA (triethylenetetraminehexaacetic acid, CAS No: 869-52-3), DO3A (1,4,7,10-tetraazacyclododecane-1,4,7-triacetic acid, CAS No: 217973-03-0), HP-DO3A (10-(2-hydroxypropyl)-1,4,7,10-tetraazacyclododecane-1,4,7-triacetic acid, CAS No: 120041-08-9), DOTA (1,4,7,10-tetraazacyclododecane-1,4,7,10-tetraacetic acid, CAS No: 60239-18-1), and known reactive derivatives thereof.

Compounds and conjugates described herein also encompass free forms and salts thereof unless otherwise specified. In this context, the "salt thereof" is a salt that can be formed by the compound or the conjugate that may form an acid-addition salt or a salt with a base depending on the type of a substituent in the compound or the conjugate. Specific examples thereof include: acid-addition salts with inorganic acids such as hydrochloric acid, hydrobromic acid, hydroiodic acid, sulfuric acid, nitric acid, and phosphoric acid, or organic acids such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditoluoyltartaric acid, citric acid, methanesulfonic acid, ethanesulfonic acid, benzenesulfonic acid, p-toluenesulfonic acid, aspartic acid, and glutamic acid; salts with inorganic bases such as sodium, potassium, magnesium, calcium, and aluminum, or organic bases such as methylamine, ethylamine, ethanolamine, lysine, and ornithine; salts with various amino acids and amino acid derivatives, such as acetylleucine; and ammonium salts. For example, DFO exists as deferoxamine methanesulfonate or exists as other salts. DTPA exits both as a free form and as sodium salt.

A certain form of the "chelating agent" for use in an MRI contrast medium is the siderophore or non-siderophore chelating agent described above.

A certain form of the "chelating agent" for use in a PET tracer is the siderophore or non-siderophore chelating agent described above. A certain form is MAG3. A certain form is DFO.

Examples of a certain form of the "chelating agent" constituting the ligand contained in the conjugate of the present invention include DFO, DTPA, DTPA-BMA, EOB-DTPA, DO3A, HP-DO3A, and DOTA. A certain form is DFO, DTPA, or DOTA. A certain form is DFO.

The "linker is a group that creates a distance between the anti-human CEACAM5 antibody Fab fragment and the ligand. Examples of a certain form of the "linker" in the conjugate include the following formula:

[Chemical Formula 6]

(hereinafter, referred to as —C(=S)—NH-(1,4-phenylene)-NH—C(=S)—), —CH$_2$-(1,4-phenylene)-NH—C(=S)—, and —C(=O)—(C$_{1-20}$ alkylene)-C(=O)—. In this context, the "C$_{1-20}$ alkylene" is linear or branched alkylene having 1 to 20 carbon atoms. A certain form of the C$_{1-20}$ alkylene is C$_{1-10}$ alkylene or C$_{1-2}$ alkylene. A certain form of the C$_{1-20}$ alkylene is ethylene. A certain form is —C(=S)—NH-(1,4-phenylene)-NH—C(=S)—. A certain form is —C(=O)—C$_2$H$_4$—C(=O)—. Examples of a reagent that can be used for forming the linker include HO—C(=O)—(C$_{1-20}$ alkylene)-C(=O)—OH, succinic acid, and p-phenylene diisothiocyanate.

The conjugate of the present invention comprising a fluorescent dye can be used as a fluorescently labeled molecular imaging agent.

A dye having absorption maximum and emission maximum at a near-infrared wavelength (650 to 1000 nm) usually used in photoimaging can be used as the fluorescent dye for use in the conjugate of the present invention. Examples of a certain form of the fluorescent dye include cyanine and indocyanine compounds. Examples of a certain form include IRDye800CW (LI-COR, Inc.), Cy (Molecular Probes, Inc.), Alexa Fluor, BODIPY, and DyLight (Thermo Fisher Scientific Inc.), CF790 (Biotium, Inc.), DY (Dyomics GmbH), HiLyte Fluor 680 and HiLyte Fluor 750 (AnaSpec Inc.), and PULSAR650 and QUASAR670 (LGC Biosearch Technologies). A certain form is IRDye800CW. The fluorescent dye can be reacted via its carboxy group, hydroxy group, amino group, or the like or via an active group introduced by a method usually used by those skilled in the art with the Fab fragment or the linker. A certain form of the fluorescent dye having an introduced active group is a fluorescent dye esterified with a N-hydroxysuccinimide (NHS) group. For example, NHS esters of IRDye800CW mentioned above are commercially available, and they can be utilized.

The conjugate of the present invention comprising a non-metal radioisotope can be used as a PET tracer.

Examples of the non-metal radioisotope for use in the conjugate of the present invention include $^{18}$F, $^{15}$O, and $^{13}$N. A certain form is $^{18}$F. For example, N-succinimidyl-4-[$^{18}$F]fluorobenzoic acid ([$^{18}$F]SFB) can be used for the binding of a compound comprising the non-metal radioisotope.

The binding of the anti-human CEACAM5 antibody Fab fragment of the present invention to the labeling moiety can be appropriately performed by those skilled in the art using a known approach. For example, the labeling moiety can be bound to one or more amino groups (e.g., an N-terminal amino group and an amino group of an amino acid side chain), one or more thiol groups (e.g., a thiol group of an amino acid side chain), or one or more carboxyl groups (e.g., carboxyl groups of the C terminus and an amino acid side chain) of the anti-human CEACAM5 antibody Fab fragment of the present invention. A certain form of the conjugate of the present invention is a conjugate in which the labeling moiety is bound to one or more amino groups of the anti-human CEACAM5 antibody Fab fragment of the present invention.

When the labeling moiety is a ligand and a linker, the conjugate of the present invention may be produced by reacting the chelating agent forming the ligand with a substance obtained through the reaction of the anti-human CEACAM5 antibody Fab fragment of the present invention with the linker. It may be produced by reacting the anti-human CEACAM5 antibody Fab fragment of the present invention with a substance obtained through the reaction of the chelating agent forming the ligand with the linker. As a reaction example, a substance obtained through the reaction of the amino group of the chelating agent with the linker is reacted with one or more amino groups (e.g., an N-terminal amino group and an amino group of a lysine side chain) of the anti-human CEACAM5 antibody Fab fragment of the present invention. When the labeling moiety is a ligand, it may be produced by reacting the chelating agent forming the ligand with the anti-human CEACAM5 antibody Fab fragment of the present invention. As a reaction example, the chelating agent is reacted with one or more amino groups (e.g., an N-terminal amino group and an amino group of a lysine side chain) of the anti-human CEACAM5 antibody Fab fragment of the present invention. Reaction of synthesizing thiourea by adding isothiocyanate to amine, reaction of synthesizing amide by adding carboxylic acid to amine, or the like can be used in the production of the conjugate of the present invention. The reaction can be performed by the application of a method known to those skilled in the art. A compound of the ligand bound to the linker in advance may be used as a starting material. Examples of the compound of the ligand bound to the linker include p-SCN-Bn-DFO (DFO substituted by a p-isothiocyanophenylaminothiocarbonyl group, CAS No: 1222468-90-7) represented by the following formula:

labeling moiety thus produced by the production method to obtain the conjugate of the present invention comprising the metal.

The conjugate of the present invention is a conjugate comprising the anti-human CEACAM5 antibody Fab fragment of the present invention bound to at least one labeling moiety. A certain form of the conjugate of the present invention is the anti-human CEACAM5 antibody Fab fragment bound to 1 to 25 labeling moieties. A certain form is the anti-human CEACAM5 antibody Fab fragment bound to 1 to 23 labeling moieties. A certain form is the anti-human CEACAM5 antibody Fab fragment bound to 1 to 16 labeling moieties. A certain form is the anti-human CEACAM5 antibody Fab fragment bound to 1 to 11 labeling moieties. A certain form is the anti-human CEACAM5 antibody Fab fragment bound to 1 to 10 labeling moieties. A certain form is the anti-human CEACAM5 antibody Fab fragment bound to 1 to 9 labeling moieties. A certain form is the anti-human CEACAM5 antibody Fab fragment bound to 4 to 23 labeling moieties. A certain form is the anti-human CEACAM5 antibody Fab fragment bound to 4 to 16 labeling moieties. A certain form is the anti-human CEACAM5 antibody Fab fragment bound to 4 to 10 labeling moieties. A certain form is the anti-human CEACAM5 antibody Fab fragment bound to 4 to 9 labeling moieties. A certain form is the anti-human CEACAM5 antibody Fab fragment bound to 3 to 23 labeling moieties. A certain form is the anti-human CEACAM5 antibody Fab fragment bound to 3 to 16 labeling moieties. A certain form is the anti-human CEACAM5 antibody Fab fragment bound to 3 to 10 labeling moieties. A certain form is the anti-human CEACAM5 antibody Fab fragment bound to 3 to 9 labeling moieties. A certain form of the conjugate of the present invention is the anti-human CEACAM5

[Chemical Formula 7]

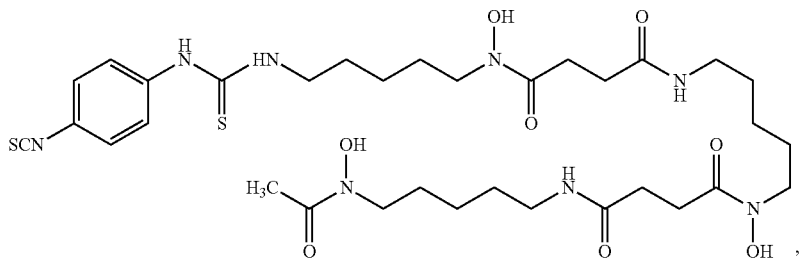

DTPA substituted by a p-isothiocyanobenzyl group (p-SCN-Bn-DTPA, CAS No: 102650-30-6), DOTA substituted by a p-isothiocyanobenzyl group (p-SCN-Bn-DOTA, CAS No: 127985-74-4), and p-SCN-Bn-CHX-A"-DTPA ([(R)-2-amino-3-(4-isothiocyanatophenyl)propyl]-trans-(S,S)-cyclohexane-1,2-diamine-pentaacetic acid, CAS No: 157380-45-5).

The conjugate of the present invention can be produced as, for example, a conjugate comprising the Fab fragment bound to at least one labeling moiety via amino groups by reacting one or more amino groups (e.g., an N-terminal amino group and an amino group of an amino acid side chain) of the anti-human CEACAM5 antibody Fab fragment of the present invention with the labeling moiety having an isocyanic acid group.

The metal (paramagnetic metal ion or metal radioisotope) can be added to the anti-human CEACAM5 antibody Fab fragment of the present invention bound to at least one antibody Fab fragment bound to at least one labeling moiety further comprising a metal. A certain form of the conjugate of the present invention may be a mixture of conjugates differing in the number of bound labeling moieties.

In one embodiment, the conjugate of the present invention is a conjugate comprising a labeling moiety and the anti-human CEACAM5 antibody Fab fragment of the present invention.

In a certain embodiment, the conjugate of the present invention is a conjugate wherein the labeling moiety is (i) a ligand and a linker, or (ii) a ligand.

In a certain embodiment, the conjugate of the present invention is a conjugate wherein the labeling moiety is (i) a ligand and a linker, or (ii) a ligand, and the ligand is a ligand represented by the following formula (A):

[Chemical Formula 8]

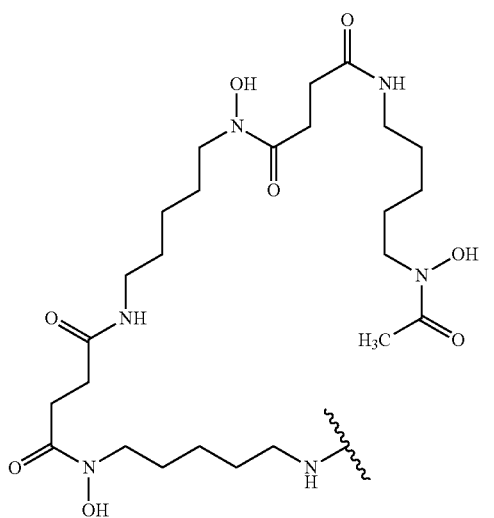

(A)

wherein the wavy line represents binding to the anti-human CEACAM5 antibody Fab fragment or the linker.

In a certain embodiment, the conjugate of the present invention is a conjugate wherein the labeling moiety is (i) a ligand and a linker, and the ligand and the linker are a group represented by the following formula (A'):

[Chemical Formula 9]

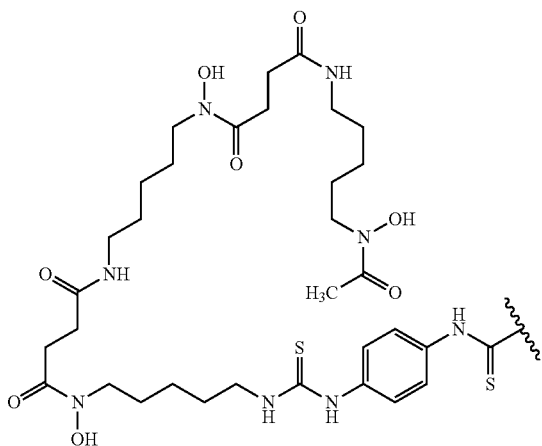

(A')

wherein the wavy line represents binding to the anti-human CEACAM5 antibody Fab fragment.

In a certain embodiment, the conjugate of the present invention is a conjugate wherein the labeling moiety is a group represented by formula (A'), and the anti-human CEACAM5 antibody Fab fragment is bound to the carbon atom of a labeling moiety terminal C(=S) group via an amino group in the Fab fragment.

In a certain embodiment, the conjugate of the present invention is a conjugate represented by the following formula (I):

(L-X)$_p$-Ab  (I)

wherein Ab is the anti-human CEACAM5 antibody Fab fragment of the present invention;
L is the ligand;
X is the linker or a bond; and
p is a natural number of 1 to 25.

A certain form of p is a natural number of 1 to 23. A certain form is a natural number of 1 to 16. A certain form is a natural number of 1 to 11. A certain form is a natural number of 1 to 10. A certain form is a natural number of 1 to 9. A certain form is a natural number of 4 to 23. A certain form is a natural number of 4 to 16. A certain form is a natural number of 4 to 10. A certain form is a natural number of 4 to 9. A certain form is a natural number of 3 to 23. A certain form is a natural number of 3 to 16. A certain form is a natural number of 3 to 10. A certain form is a natural number of 3 to 9.

In a certain embodiment, the conjugate of the present invention is a conjugate of formula (I) wherein L is a ligand represented by the following formula (A):

[Chemical Formula 10]

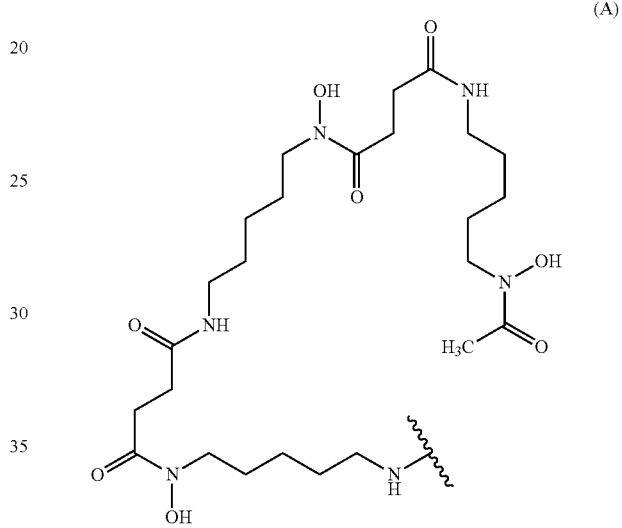

(A)

wherein the wavy line represents binding to X (or Ab when X is a bond).

In a certain embodiment, the conjugate of formula (I) is a conjugate represented by the following formula (II):

[Chemical Formula 11]

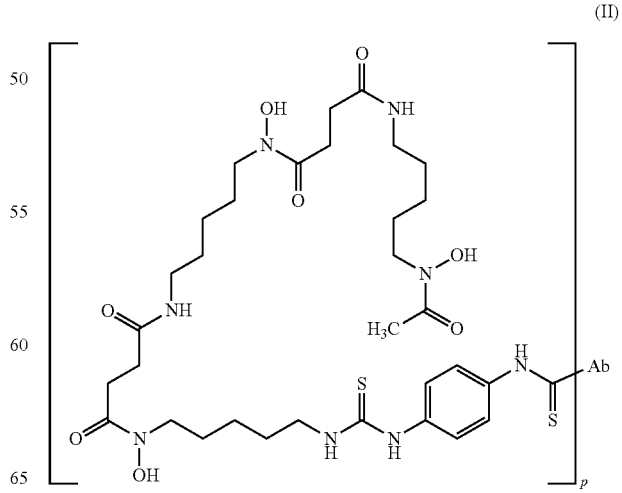

(II)

wherein Ab is the anti-human CEACAM5 antibody Fab fragment of the present invention; and
p is a natural number of 1 to 25.

A certain form of p is a natural number of 1 to 23. A certain form is a natural number of 1 to 16. A certain form is a natural number of 1 to 11. A certain form is a natural number of 1 to 10. A certain form is a natural number of 1 to 9. A certain form is a natural number of 4 to 23. A certain form is a natural number of 4 to 16. A certain form is a natural number of 4 to 10. A certain form is a natural number of 4 to 9. A certain form is a natural number of 3 to 23. A certain form is a natural number of 3 to 16. A certain form is a natural number of 3 to 10. A certain form is a natural number of 3 to 9.

Ab is bound to the carbon atom of labeling moiety terminal C(=S) via an amino group in the Ab.

In a certain embodiment, the conjugate of the present invention is a conjugate of formula (I) further comprising a metal. A certain form of the metal is a metal radioisotope. A certain form of the metal radioisotope is $^{89}$Zr.

In a certain embodiment, the conjugate of the present invention is a conjugate of formula (II) further comprising a metal. A certain form of the metal is a metal radioisotope. A certain form of the metal radioisotope is $^{89}$Zr.

The conjugate of the present invention also includes a conjugate which is a mixture of a plurality of conjugates. For example, a conjugate which is mixture of a conjugate comprising a labeling moiety and a non-posttranslationally-modified anti-human CEACAM5 antibody Fab fragment of the present invention, and a conjugate comprising a labeling moiety and the anti-human CEACAM5 antibody Fab fragment of the present invention resulting from the posttranslational modification of the anti-human CEACAM5 antibody Fab fragment is also included in the conjugate of the present invention.

Certain embodiments of the conjugate of the present invention which is a mixture of a plurality of conjugates of the present invention will be shown below.

(1) A conjugate which is a mixture of a conjugate wherein the labeling moiety is a ligand and a linker represented by formula (A'), and the anti-human CEACAM5 antibody Fab fragment is an anti-human CEACAM5 antibody Fab fragment comprising a heavy chain fragment consisting of the amino acid sequence represented by SEQ ID NO: 2 and a light chain consisting of the amino acid sequence represented by SEQ ID NO: 4, and a conjugate wherein the labeling moiety is a ligand and a linker represented by formula (A'), and the anti-human CEACAM5 antibody Fab fragment is an anti-human CEACAM5 antibody Fab fragment comprising a heavy chain fragment derived from a heavy chain fragment consisting of the amino acid sequence represented by SEQ ID NO: 2 by the modification of glutamine at amino acid position 1 of SEQ ID NO: 2 into pyroglutamic acid, and a light chain consisting of the amino acid sequence represented by SEQ ID NO: 4.

(2) The conjugate of (1), further comprising a metal.

(3) A conjugate which is a mixture of a conjugate of (1) further comprising a metal and a conjugate of (1) comprising no metal.

(4) The conjugate of (2) or (3), wherein the metal is a metal radioisotope.

(5) The conjugate of (4), wherein the metal radioisotope is $^{89}$Zr.

<Polynucleotide of Present Invention>

The polynucleotide of the present invention includes a polynucleotide comprising a nucleotide sequence encoding the heavy chain fragment of the anti-human CEACAM5 antibody Fab fragment of the present invention, and a polynucleotide comprising a nucleotide sequence encoding the light chain of the anti-human CEACAM5 antibody Fab fragment of the present invention.

In one embodiment, the polynucleotide of the present invention is a polynucleotide comprising a nucleotide sequence encoding a heavy chain fragment comprising a heavy chain variable region consisting of the amino acid sequence represented by amino acid positions 1 to 121 of SEQ ID NO: 2, or a polynucleotide comprising a nucleotide sequence encoding a light chain comprising a light chain variable region consisting of the amino acid sequence represented by amino acid positions 1 to 112 of SEQ ID NO: 4.

Examples of the polynucleotide comprising a nucleotide sequence encoding a heavy chain fragment comprising a heavy chain variable region consisting of the amino acid sequence represented by amino acid positions 1 to 121 of SEQ ID NO: 2 include a polynucleotide comprising a nucleotide sequence from nucleotide positions 1 to 363 of SEQ ID NO: 1.

Examples of the polynucleotide comprising a nucleotide sequence encoding a light chain comprising a light chain variable region consisting of an amino acid sequence from amino acid positions 1 to 112 of SEQ ID NO: 4 include a polynucleotide comprising a nucleotide sequence from nucleotide positions 1 to 336 of SEQ ID NO: 3.

In a preferred embodiment, the polynucleotide of the present invention is a polynucleotide comprising a nucleotide sequence encoding a heavy chain fragment consisting of the amino acid sequence represented by SEQ ID NO: 2, or a polynucleotide comprising a nucleotide sequence encoding a light chain consisting of the amino acid sequence represented by SEQ ID NO: 4.

Examples of the polynucleotide comprising a nucleotide sequence encoding a heavy chain fragment consisting of the amino acid sequence represented by SEQ ID NO: 2 include a polynucleotide comprising the nucleotide sequence represented by SEQ ID NO: 1.

Examples of the polynucleotide comprising a nucleotide sequence encoding a light chain consisting of the amino acid sequence represented by SEQ ID NO: 4 include a polynucleotide comprising the nucleotide sequence represented by SEQ ID NO: 3.

The polynucleotide of the present invention is synthesizable through the use of a gene synthesis method known in the art on the basis of nucleotide sequences designed from the amino acid sequences of the heavy chain fragment and the light chain of the anti-human CEACAM5 antibody Fab fragment of the present invention. Various methods known to those skilled in the art, such as methods for synthesizing an antibody gene described in International Publication No. WO 90/07861 can be used as such gene synthesis methods.

<Expression Vector of Present Invention>

The expression vector of the present invention includes an expression vector comprising a polynucleotide comprising a nucleotide sequence encoding the heavy chain fragment of the anti-human CEACAM5 antibody Fab fragment of the present invention, an expression vector comprising a polynucleotide comprising a nucleotide sequence encoding the light chain of the anti-human CEACAM5 antibody Fab fragment of the present invention, and an expression vector comprising a polynucleotide comprising a nucleotide sequence encoding the heavy chain fragment of the anti-human CEACAM5 antibody Fab fragment of the present invention and a polynucleotide comprising a nucleotide sequence encoding the light chain of the anti-human CEACAM5 antibody Fab fragment of the present invention.

The expression vector of the present invention preferably includes an expression vector comprising a polynucleotide comprising a nucleotide sequence encoding a heavy chain fragment comprising a heavy chain variable region consisting of the amino acid sequence represented by amino acid positions 1 to 121 of SEQ ID NO: 2, an expression vector comprising a polynucleotide comprising a nucleotide sequence encoding a light chain comprising a light chain variable region consisting of the amino acid sequence represented by amino acid positions 1 to 112 of SEQ ID NO: 4, and an expression vector comprising a polynucleotide comprising a nucleotide sequence encoding a heavy chain fragment comprising a heavy chain variable region consisting of the amino acid sequence represented by amino acid positions 1 to 121 of SEQ ID NO: 2 and a polynucleotide comprising a nucleotide sequence encoding a light chain comprising a light chain variable region consisting of the amino acid sequence represented by amino acid positions 1 to 112 of SEQ ID NO: 4.

The expression vector of the present invention preferably includes an expression vector comprising a polynucleotide comprising a nucleotide sequence encoding a heavy chain fragment consisting of the amino acid sequence represented by SEQ ID NO: 2, an expression vector comprising a polynucleotide comprising a nucleotide sequence encoding a light chain consisting of the amino acid sequence represented by SEQ ID NO: 4, and an expression vector comprising a polynucleotide comprising a nucleotide sequence encoding a heavy chain fragment consisting of the amino acid sequence represented by SEQ ID NO: 2 and a polynucleotide comprising a nucleotide sequence encoding a light chain consisting of the amino acid sequence represented by SEQ ID NO: 4.

The expression vector of the present invention is not particularly limited as long as a polypeptide encoded by the polynucleotide of the present invention can be produced in various host cells of prokaryotic cells and/or eukaryotic cells. Examples of such an expression vector include plasmid vectors and virus vectors (e.g., adenovirus and retrovirus). Preferably, pEE6.4 or pEE12.4 (Lonza Group AG) can be used.

The expression vector of the present invention may comprise a promoter operably linked to a gene encoding the heavy chain fragment and/or the light chain in the polynucleotide of the present invention. Examples of the promoter for expressing the Fab fragment of the present invention in a host cell include Trp promoter, lac promoter, recA promoter, λPL promoter, lpp promoter, and tac promoter when the host cell is a bacterium of the genus *Escherichia*. Examples of the promoter for expression in yeasts include PH05 promoter, PGK promoter, GAP promoter, and ADH promoter. Examples of the promoter for expression in bacteria of the genus *Bacillus* include SL01 promoter, SP02 promoter, and penP promoter. Examples thereof include promoters derived from viruses such as CMV, RSV, and SV40, retrovirus promoter, actin promoter, EF (elongation factor) 1α promoter, and heat shock promoter when the host is a eukaryotic cell such as a mammalian cell.

In the case of using a bacterium, particularly, *E. coli*, as a host cell, the expression vector of the present invention may further comprise a start codon, a stop codon, a terminator region and a replicable unit. On the other hand, in the case of using a yeast, an animal cell or an insect cell as a host, the expression vector of the present invention may comprise a start codon and a stop codon. In this case, an enhancer sequence, 5' and 3' untranslated regions of a gene encoding the heavy chain fragment and/or the light chain of the present invention, a secretion signal sequence, a splicing junction, a polyadenylation site, or a replicable unit, etc. may be contained therein. Also, a selective marker usually used (e.g., tetracycline resistance gene, ampicillin resistance gene, kanamycin resistance gene, neomycin resistance gene, and dihydrofolate reductase gene) may be contained therein according to a purpose.

<Transformed Host Cell of Present Invention>

The transformed host cell of the present invention includes a host cell transformed with the expression vector of the present invention, selected from the group consisting of the following (a) to (d):

(a) a host cell transformed with an expression vector comprising a polynucleotide comprising a nucleotide sequence encoding the heavy chain fragment of the anti-human CEACAM5 antibody Fab fragment of the present invention;

(b) a host cell transformed with an expression vector comprising a polynucleotide comprising a nucleotide sequence encoding the light chain of the anti-human CEACAM5 antibody Fab fragment of the present invention;

(c) a host cell transformed with an expression vector comprising a polynucleotide comprising a nucleotide sequence encoding the heavy chain fragment of the anti-human CEACAM5 antibody Fab fragment of the present invention and a polynucleotide comprising a nucleotide sequence encoding the light chain of the anti-human CEACAM5 antibody Fab fragment of the present invention; and (d) a host cell transformed with an expression vector comprising a polynucleotide comprising a nucleotide sequence encoding the heavy chain fragment of the anti-human CEACAM5 antibody Fab fragment of the present invention and an expression vector comprising a polynucleotide comprising a nucleotide sequence encoding the light chain of the anti-human CEACAM5 antibody Fab fragment of the present invention.

In one embodiment, the transformed host cell of the present invention is a host cell transformed with the expression vector of the present invention, selected from the group consisting of the following (a) to (d):

(a) a host cell transformed with an expression vector comprising a polynucleotide comprising a nucleotide sequence encoding a heavy chain fragment comprising a heavy chain variable region consisting of the amino acid sequence represented by amino acid positions 1 to 121 of SEQ ID NO: 2;

(b) a host cell transformed with an expression vector comprising a polynucleotide comprising a nucleotide sequence encoding a light chain comprising a light chain variable region consisting of the amino acid sequence represented by amino acid positions 1 to 112 of SEQ ID NO: 4;

(c) a host cell transformed with an expression vector comprising a polynucleotide comprising a nucleotide sequence encoding a heavy chain fragment comprising a heavy chain variable region consisting of the amino acid sequence represented by amino acid positions 1 to 121 of SEQ ID NO: 2 and a polynucleotide comprising a nucleotide sequence encoding a light chain comprising a light chain variable region consisting of the amino acid sequence represented by amino acid positions 1 to 112 of SEQ ID NO: 4; and (d) a host cell transformed with an expression vector comprising a polynucleotide comprising a nucleotide sequence encoding a heavy chain fragment comprising a heavy chain variable region consisting of the amino acid sequence represented by amino acid positions 1 to 121 of SEQ ID NO: 2 and an expression vector comprising a polynucleotide comprising a nucleotide sequence encoding a light chain comprising a light chain variable region consisting of the amino acid sequence represented by amino acid positions 1 to 112 of SEQ ID NO: 4.

In one embodiment, the transformed host cell of the present invention is a host cell transformed with the expression vector of the present invention, selected from the group consisting of the following (a) to (d):
(a) a host cell transformed with an expression vector comprising a polynucleotide comprising a nucleotide sequence encoding a heavy chain fragment consisting of the amino acid sequence represented by SEQ ID NO: 2;
(b) a host cell transformed with an expression vector comprising a polynucleotide comprising a nucleotide sequence encoding a light chain consisting of the amino acid sequence represented by SEQ ID NO: 4;
(c) a host cell transformed with an expression vector comprising a polynucleotide comprising a nucleotide sequence encoding a heavy chain fragment consisting of the amino acid sequence represented by SEQ ID NO: 2 and a polynucleotide comprising a nucleotide sequence encoding a light chain consisting of the amino acid sequence represented by SEQ ID NO: 4; and
(d) a host cell transformed with an expression vector comprising a polynucleotide comprising a nucleotide sequence encoding a heavy chain fragment consisting of the amino acid sequence represented by SEQ ID NO: 2 and an expression vector comprising a polynucleotide comprising a nucleotide sequence encoding a light chain consisting of the amino acid sequence represented by SEQ ID NO: 4.

Preferred examples of the transformed host cell of the present invention include a host cell transformed with an expression vector comprising a polynucleotide comprising a nucleotide sequence encoding the heavy chain fragment of the anti-human CEACAM5 antibody Fab fragment of the present invention and a polynucleotide comprising a nucleotide sequence encoding the light chain of the anti-human CEACAM5 antibody Fab fragment of the present invention, and a host cell transformed with an expression vector comprising a polynucleotide comprising a nucleotide sequence encoding the heavy chain fragment of the anti-human CEACAM5 antibody Fab fragment of the present invention and an expression vector comprising a polynucleotide comprising a nucleotide sequence encoding the light chain of the anti-human CEACAM5 antibody Fab fragment of the present invention.

The host cell to be transformed is not particularly limited as long as it is compatible with the expression vector used and can be transformed with the expression vector to express the Fab fragment. Examples thereof include various cells such as natural cells and artificially established cells usually used in the technical field of the present invention (e.g., bacteria (bacteria of the genus *Escherichia* and bacteria of the genus *Bacillus*), yeasts (the genus *Saccharomyces*, the genus *Pichia*, etc.), animal cells and insect cells (e.g., Sf9)), and mammalian cell lines (e.g., cultured cells such as CHOK1SV cells, CHO-DG44 cells, and 293 cells). The transformation itself can be performed by a known method, for example, a calcium phosphate method or an electroporation method.

<Method for Producing Anti-Human CEACAM5 Antibody Fab Fragment According to Present Invention>

The method for producing an anti-human CEACAM5 antibody Fab fragment according to the present invention comprises the step of culturing the transformed host cell of the present invention to express the anti-human CEACAM5 antibody Fab fragment.

In one embodiment, the transformed host cell of the present invention to be cultured in the method for producing an anti-human CEACAM5 antibody Fab fragment according to the present invention is selected from the group consisting of the following (a) to (c):
(a) a host cell transformed with an expression vector comprising a polynucleotide comprising a nucleotide sequence encoding the heavy chain fragment of the anti-human CEACAM5 antibody Fab fragment of the present invention and a polynucleotide comprising a nucleotide sequence encoding the light chain of the anti-human CEACAM5 antibody Fab fragment of the present invention;
(b) a host cell transformed with an expression vector comprising a polynucleotide comprising a nucleotide sequence encoding the heavy chain fragment of the anti-human CEACAM5 antibody Fab fragment of the present invention and an expression vector comprising a polynucleotide comprising a nucleotide sequence encoding the light chain of the anti-human CEACAM5 antibody Fab fragment of the present invention; and
(c) a host cell transformed with an expression vector comprising a polynucleotide comprising a nucleotide sequence encoding the heavy chain fragment of the anti-human CEACAM5 antibody Fab fragment of the present invention, and a host cell transformed with an expression vector comprising a polynucleotide comprising a nucleotide sequence encoding the light chain of the anti-human CEACAM5 antibody Fab fragment of the present invention.

A certain form of the transformed host cell of the present invention to be cultured in the method for producing an anti-human CEACAM5 antibody Fab fragment according to the present invention is selected from the group consisting of the following (a) to (c):
(a) a host cell transformed with an expression vector comprising a polynucleotide comprising a nucleotide sequence encoding a heavy chain fragment comprising a heavy chain variable region consisting of the amino acid sequence represented by amino acid positions 1 to 121 of SEQ ID NO: 2 and a polynucleotide comprising a nucleotide sequence encoding a light chain comprising a light chain variable region consisting of the amino acid sequence represented by amino acid positions 1 to 112 of SEQ ID NO: 4;
(b) a host cell transformed with an expression vector comprising a polynucleotide comprising a nucleotide sequence encoding a heavy chain fragment comprising a heavy chain variable region consisting of the amino acid sequence represented by amino acid positions 1 to 121 of SEQ ID NO: 2 and an expression vector comprising a polynucleotide comprising a nucleotide sequence encoding a light chain comprising a light chain variable region consisting of the amino acid sequence represented by amino acid positions 1 to 112 of SEQ ID NO: 4; and
(c) a host cell transformed with an expression vector comprising a polynucleotide comprising a nucleotide sequence encoding a heavy chain fragment comprising a heavy chain variable region consisting of the amino acid sequence represented by amino acid positions 1 to 121 of SEQ ID NO: 2, and a host cell transformed with an expression vector comprising a polynucleotide comprising a nucleotide sequence encoding a light chain comprising a light chain variable region consisting of the amino acid sequence represented by amino acid positions 1 to 112 of SEQ ID NO: 4.

A certain form of the transformed host cell of the present invention to be cultured in the method for producing an anti-human CEACAM5 antibody Fab fragment according to the present invention is selected from the group consisting of the following (a) to (c):
(a) a host cell transformed with an expression vector comprising a polynucleotide comprising a nucleotide sequence encoding a heavy chain fragment consisting of the amino acid sequence represented by SEQ ID NO: 2 and a polynucleotide comprising a nucleotide sequence encoding a light chain consisting of the amino acid sequence represented by SEQ ID NO: 4;
(b) a host cell transformed with an expression vector comprising a polynucleotide comprising a nucleotide sequence encoding a heavy chain fragment consisting of the amino acid sequence represented by SEQ ID NO: 2 and an expression vector comprising a polynucleotide comprising a nucleotide sequence encoding a light chain consisting of the amino acid sequence represented by SEQ ID NO: 4; and
(c) a host cell transformed with an expression vector comprising a polynucleotide comprising a nucleotide sequence encoding a heavy chain fragment consisting of the amino acid sequence represented by SEQ ID NO: 2, and a host cell transformed with an expression vector comprising a polynucleotide comprising a nucleotide sequence encoding a light chain consisting of the amino acid sequence represented by SEQ ID NO: 4.

The transformed host cell of the present invention used is preferably a host cell transformed with an expression vector comprising a polynucleotide comprising a nucleotide sequence encoding the heavy chain fragment of the anti-human CEACAM5 antibody Fab fragment of the present invention and a polynucleotide comprising a nucleotide sequence encoding the light chain of the anti-human CEACAM5 antibody Fab fragment of the present invention, or a host cell transformed with an expression vector comprising a polynucleotide comprising a nucleotide sequence encoding the heavy chain fragment of the anti-human CEACAM5 antibody Fab fragment of the present invention and an expression vector comprising a polynucleotide comprising a nucleotide sequence encoding the light chain of the anti-human CEACAM5 antibody Fab fragment of the present invention.

In the method for producing an anti-human CEACAM5 antibody Fab fragment according to the present invention, the transformed host cell can be cultured in a nutrient medium. The nutrient medium preferably contains a carbon source, an inorganic nitrogen source or an organic nitrogen source necessary for the growth of the transformed host cell. Examples of the carbon source include glucose, dextran, soluble starch, and sucrose. Examples of the inorganic nitrogen source or the organic nitrogen source include ammonium salts, nitrates, amino acids, corn steep liquor, peptone, casein, meat extracts, soymeal, and potato extracts. Also, other nutrients (e.g., inorganic salts (e.g., calcium chloride, sodium dihydrogen phosphate, and magnesium chloride), vitamins, and antibiotics (e.g., tetracycline, neomycin, ampicillin, and kanamycin)) may be contained therein, if desired.

The culture itself of the transformed host cell is performed by a known method. Culture conditions, for example, temperature, medium pH and culture time, are appropriately selected. When the host is, for example, an animal cell, MEM medium (Science; 1952; 122: 501), DMEM medium (Virology; 1959; 8: 396-97), RPMI1640 medium (J. Am. Med. Assoc.; 1967; 199: 519-24), 199 medium (Proc. Soc. Exp. Biol. Med.; 1950; 73:1-8), or the like containing approximately 5 to 20% fetal bovine serum can be used as a medium. The medium pH is preferably approximately 6 to 8. The culture is usually performed at approximately 30 to 40° C. for approximately 15 to 336 hours, and aeration or stirring can also be performed, if necessary. When the host is an insect cell, examples thereof include Grace's medium (PNAS; 1985; 82: 8404-8) containing fetal bovine serum. Its pH is preferably approximately 5 to 8. The culture is usually performed at approximately 20 to 40° C. for 15 to 100 hours, and aeration or stirring can also be performed, if necessary. When the host is a bacterium, an actinomycete, a yeast, or a filamentous fungus, for example, a liquid medium containing the nutrient source described above is appropriate. A medium of pH 5 to 8 is preferred. When the host is *E. coli*, preferred examples of the medium include LB medium and M9 medium (Miller et al., Exp. Mol. Genet, Cold Spring Harbor Laboratory; 1972: 431). In such a case, the culture can usually be performed at 14 to 43° C. for approximately 3 to 24 hours with aeration or stirring, if necessary. When the host is a bacterium of the genus *Bacillus*, it can usually be performed at 30 to 40° C. for approximately 16 to 96 hours with aeration or stirring, if necessary. When the host is a yeast, examples of the medium include Burkholder minimum medium (PNAS; 1980; 77: 4505-8). Its pH is desirably 5 to 8. The culture is usually performed at approximately 20 to 35° C. for approximately 14 to 144 hours, and aeration or stirring can also be performed, if necessary.

The method for producing an anti-human CEACAM5 antibody Fab fragment according to the present invention can comprise the step of recovering, preferably isolating or purifying, the expressed anti-human CEACAM5 antibody Fab fragment, in addition to the step of culturing the transformed host cell of the present invention to express the anti-human CEACAM5 antibody Fab fragment. Examples of the isolation or purification method include: methods exploiting solubility, such as salting out and a solvent precipitation method; methods exploiting difference in molecular weight, such as dialysis, ultrafiltration, gel filtration, and sodium dodecyl sulfate-polyacrylamide gel electrophoresis; methods exploiting charge, such as ion-exchange chromatography and hydroxylapatite chromatography; methods exploiting specific affinity, such as affinity chromatography; methods exploiting difference in hydrophobicity, such as reverse-phase high-performance liquid chromatography; and methods exploiting difference in isoelectric point, such as isoelectric focusing.

<Method for Producing Conjugate According to Present Invention>

The method for producing a conjugate according to the present invention comprises the step of covalently binding the anti-human CEACAM5 antibody Fab fragment of the present invention to a labeling moiety. The method for producing a conjugate according to the present invention may also comprise the steps of: culturing the transformed host cell of the present invention to express the anti-human CEACAM5 antibody Fab fragment; and covalently binding the Fab fragment to a labeling moiety. The method for producing a conjugate according to the present invention may also comprise the steps of: culturing the transformed host cell of the present invention to express the anti-human CEACAM5 antibody Fab fragment; recovering the expressed Fab fragment; and covalently binding the Fab fragment to a labeling moiety. The linker, ligand, or fluorescent dye, etc., and linking method used can employ those described in <Conjugate of present invention>.

In one embodiment, the method for producing a conjugate according to the present invention is a method comprising the steps of: culturing the transformed host cell of the present invention to express the anti-human CEACAM5 antibody Fab fragment; and covalently binding the Fab fragment to a labeling moiety. A certain form of the method for producing a conjugate according to the present invention is a method comprising the steps of: culturing the transformed host cell of the present invention to express the anti-human CEACAM5 antibody Fab fragment; recovering the expressed Fab fragment; and covalently binding the Fab fragment to a labeling moiety.

A certain form of the method for producing a conjugate according to the present invention is a method comprising the steps of: culturing the transformed host cell of the present invention to express the anti-human CEACAM5 antibody Fab fragment; and i) binding the Fab fragment via a linker to a ligand or ii) covalently binding the Fab fragment directly to a ligand. A certain form of the method for producing a conjugate according to the present invention is a method comprising the steps of: culturing the transformed host cell of the present invention to express the anti-human CEACAM5 antibody Fab fragment; recovering the expressed Fab fragment; and i) binding the Fab fragment via a linker to a ligand or ii) covalently binding the Fab fragment directly to a ligand.

A certain form of the method for producing a conjugate according to the present invention is a method comprising the steps of: culturing the transformed host cell of the present invention to express the anti-human CEACAM5 antibody Fab fragment; covalently binding the Fab fragment via a linker or directly to a ligand; and binding a metal to the ligand of the conjugate through a coordinate bond (i.e., forming a chelate complex). A certain form of the method for producing a conjugate according to the present invention is a method comprising the steps of: culturing the transformed host cell of the present invention to express the anti-human CEACAM5 antibody Fab fragment; recovering the expressed Fab fragment; covalently binding the Fab fragment via a linker or directly to a ligand; and binding a metal to the ligand of the conjugate through a coordinate bond.

A certain form of the method for producing a conjugate according to the present invention is a method comprising the steps of: culturing the transformed host cell of the present invention to express the anti-human CEACAM5 antibody Fab fragment; covalently binding the Fab fragment via a linker or directly to a ligand; and binding a metal radioisotope to the ligand of the conjugate through a coordinate bond (i.e., forming a chelate complex). A certain form of the method for producing a conjugate according to the present invention is a method comprising the steps of: culturing the transformed host cell of the present invention to express the anti-human CEACAM5 antibody Fab fragment; recovering the expressed Fab fragment; covalently binding the Fab fragment via a linker or directly to a ligand; and binding a metal radioisotope to the ligand of the conjugate through a coordinate bond.

The method for producing a conjugate according to the present invention may be carried out as a method comprising two or more of the steps defined above as a series of steps or may be carried out as a method comprising at least one of the steps defined above. For example, a method comprising the step of binding the anti-human CEACAM5 antibody Fab fragment of the present invention to a labeling moiety, and a method comprising the step of labeling the anti-human CEACAM5 antibody Fab fragment of the present invention bound to the labeling moiety with a metal are also included in the method for producing a conjugate according to the present invention. Also, the method for producing a conjugate according to the present invention includes a method having a different order of steps. For example, a method comprising labeling a ligand with a metal radioisotope, and then covalently binding the ligand to the anti-human CEACAM5 antibody Fab fragment of the present invention is also included in the method for producing a conjugate according to the present invention.

<Composition for Diagnosis and Diagnosis Method of Present Invention>

The present invention relates to a composition for diagnosis comprising the conjugate of the present invention comprising a fluorescent dye, a metal or a non-metal radioisotope (hereinafter, referred to as the detectable conjugate of the present invention). The detectable conjugate of the present invention can be formulated according to a routine method and utilized as a clinical staging drug (particularly, for the diagnosis of a cancer). The clinical staging drug means a diagnostic drug capable of examining the degree of progression of a medical condition. For example, for cancers, it means a diagnostic drug capable of examining the clinical stage thereof. The cancer expected to be able to be diagnosed by the composition for diagnosis of the present invention is selected from the group consisting of colorectal cancer, breast cancer, lung cancer, thyroid gland cancer and a cancer resulting from the metastasis thereof. The cancer is preferably colorectal cancer or a cancer resulting from the metastasis of colorectal cancer. The cancer is more preferably a cancer resulting from the metastasis of colorectal cancer. Such a cancer includes hepatic metastasis.

The amount of the detectable conjugate of the present invention added for the formulation of the composition for diagnosis of the present invention differs depending on the degree of symptoms or age of a patient, the dosage form of a preparation used, or the binding titer of the Fab fragment, etc. For example, approximately 0.001 mg/kg to 100 mg/kg based on the mass of the Fab fragment can be used per unit body weight of a patient.

Examples of the dosage form of the composition for diagnosis of the present invention can include parenteral agents such as injections and agents for drip infusion. Administration is preferably performed by intravenous injection, local intramuscular injection to a target, subcutaneous injection, or the like. For the formulation, a carrier or an additive suitable for these dosage forms can be used in a pharmaceutically acceptable range. The type of the pharmaceutically acceptable carrier or additive is not particularly limited, and a carrier or an additive well known to those skilled in the art can be used.

The present invention also relates to use of the detectable conjugate of the present invention for the production of a composition for diagnosis of cancer or a composition for staging in a certain form. The present invention also relates to the detectable conjugate of the present invention for use in the diagnosis of a cancer or for use in staging in a certain form.

Further, the present invention also relates to a method for diagnosing a cancer, comprising preoperatively or intraoperatively administering the detectable conjugate of the present invention to a subject. In this context, the "subject" is a human or any of other mammals in need of receiving the diagnosis. A certain form is a human in need of receiving the diagnosis. The effective amount of the detectable conjugate of the present invention in the diagnosis method of the present invention may be the same amount as the effective amount of the detectable conjugate of the present invention for the formulation described above. In the diagnosis method of the present invention, the detectable conjugate of the present invention is preferably administered by intravenous injection or the like. The conjugate of the present invention for use as a PET tracer can be photographed by PET after 1.5 to 48 hours, after 2 to 48 hours in a certain form, after 4 to 24 hours in a certain form, after 4 to 6 hours in a certain form, or after 1.5 to 6 hours in a certain form from administration. In the diagnosis method of the present invention, in the case of using a fluorescence-labeled conjugate of the present invention in intraoperative diagnosis, the conjugate is administered to a patient, for example, 2 to 48 hours, preferably 4 hours, before operation.

In an alternative embodiment, the present invention also relates to use of the anti-human CEACAM5 antibody Fab fragment of the present invention for the production of the conjugate of the present invention. In a certain embodiment, the present invention also relates to use of the anti-human CEACAM5 antibody Fab fragment of the present invention for the production of a composition for diagnosis comprising the conjugate of the present invention.

The present invention is generally described above. Particular Examples will be provided here for reference in order to obtain further understanding. However, these are given for illustrative purposes and do not limit the present invention.

EXAMPLES

Example 1: Preparation of Anti-Human CEACAM5 Antibody Fab Fragment

An antibody having variable regions expected not to attenuate affinity even by the binding of a labeling moiety was designed using a molecular model of a humanized antibody constructed in accordance with the literature (Proteins: Structure, Function, and Bioinformatics; 2014; 82: 1624-1635) after humanization of mouse-derived anti-human CEACAM5 antibody T84.66 with reference to the method described in the literature (Protein Eng. Des. Sel.; 2004; 17: 481-489).

A gene encoding a signal sequence (Protein Engineering; 1987; 1: 499-505) and a human Igγ1 Fab region gene (consisting of a nucleotide sequence from nucleotide positions 364 to 678 of SEQ ID NO: 1) were connected to the 5' side and the 3' side, respectively, of the heavy chain variable region gene of the antibody, and this heavy chain fragment gene was inserted to GS vector pEE6.4 (Lonza Group AG). Also, a gene encoding a signal sequence and a human Igκ constant region gene (consisting of a nucleotide sequence from nucleotide positions 337 to 657 of SEQ ID NO: 3) were connected to the 5' side and the 3' side, respectively, of the light chain variable region gene of the antibody, and this light chain gene was inserted to GS vector pEE12.4 (Lonza Group AG). The aforementioned pEE vectors respectively having inserts of the heavy chain fragment and light chain genes of the antibody were cleaved with restriction enzymes NotI and PvuI and ligated using ligation kit TAKARA Ligation Kit Ver 2.1 (Takara Bio Inc.) to construct a GS vector having both the inserts of the heavy chain fragment and light chain genes.

The antibody was expressed by two types of methods, transient expression and constitutive expression, using the aforementioned GS vector having both the inserts of the heavy chain fragment and light chain genes. For the transient expression, Expi293F cells (Thermo Fisher Scientific Inc.) cultured into approximately 3000000 cells/mL in Expi293 Expression Medium (Thermo Fisher Scientific Inc.) were transfected with the aforementioned GS vector having both the inserts of the heavy chain fragment and light chain genes using ExpiFectamine 293 Transfection Kit (Thermo Fisher Scientific Inc.) and cultured for 5 to 7 days. The culture supernatant was purified using KappaSelect (GE Healthcare Japan Corp.) to obtain a Fab fragment. For the constitutive expression, CHOK1SV cells (Lonza Group AG) were transfected with a linear vector obtained with PvuI from the aforementioned GS vector having both the inserts of the heavy chain fragment and light chain genes, by electroporation using Gene Pulser (Bio-Rad Laboratories, Inc.). On the day following the transfection, methionine sulfoximine was added thereto, followed by culture for 5 to 7 days. The cells were inoculated to a semisolid medium containing methylcellulose. After colony formation, cells having a large expression level of the Fab fragment were obtained using ClonePix FL (Molecular Devices, LLC). The culture supernatant of the cells was purified using Capto L (GE Healthcare Japan Corp.), Q Sepharose Fast Flow (GE Healthcare Japan Corp.), and BioPro S75 (YMC Co., Ltd.) to obtain a Fab fragment.

The nucleotide sequence encoding the heavy chain fragment of the prepared anti-human CEACAM5 antibody Fab fragment (designated as PB009-01) is shown in SEQ ID NO: 1, and the amino acid sequence encoded thereby is shown in SEQ ID NO: 2. The nucleotide sequence encoding the light chain of PB009-01 is shown in SEQ ID NO: 3, and the amino acid sequence encoded thereby is shown in SEQ ID NO: 4. The heavy chain variable region of PB009-01 consists of an amino acid sequence from amino acid positions 1 to 121 of SEQ ID NO: 2, and heavy chain CDR1, CDR2, and CDR3 consist of amino acid sequences from amino acid positions 31 to 35, 50 to 66, and 99 to 110, respectively, of SEQ ID NO: 2. The light chain variable region of PB009-01 consists of an amino acid sequence from amino acid positions 1 to 112 of SEQ ID NO: 4, and light chain CDR1, CDR2, and CDR3 consist of amino acid sequences from amino acid positions 24 to 38, 54 to 60, and 93 to 101, respectively, of SEQ ID NO: 4.

The variable regions and the CDR sequences were determined according to the Kabat numbering (Kabat et al., 1991, Sequences of Proteins of Immunological Interest, 5th Ed., United States Public Health Service, National Institute of Health, Bethesda).

Example 2: Production of Fab Fragment Conjugate p-SCN-Bn-DFO (DFO substituted by a p-isothiocyanophenylaminothiocarbonyl group) (Macrocyclics, Inc.) was used in the binding of chelating agent DFO to Fab fragment PB009-01. A ⅕ amount of a 0.1 M sodium carbonate solution (pH 9.0) was added to a Fab fragment solution adjusted to 1 mg/mL with phosphate-buffered saline (pH 7.4). p-SCN-Bn-DFO was added thereto at a final concentration of 1 mg/mL and reacted at 37° C. for 1.5 hours. After the reaction, a Fab fragment bound to DFO via a linker (—C(=S)—NH-(1,4-phenylene)-NH—C(=S)—) (designated as PB009-02) was purified using Amicon Ultra 3K-0.5 mL centrifugal filter (Merck Millipore).

The number of ligands constituted by DFO bound to PB009-02 was confirmed by mass spectrometry. PB009-02 was desalted using MassPREP Micro Desalting Column (Waters Corp.), and measurement was carried out using SYNAPT G2 mass spectrometer (Waters Corp.). As a result, a molecule in which at least 3 to 10 ligands constituted by DFO were bound to one PB009-01 was confirmed.

Example 3: Binding Activity Evaluation

In order to measure the detailed binding activity of PB009-02, analysis was conducted by SPR. In this Example, a Fab fragment of M5A (referred to as M5A-Fab), a humanized antibody of T84.66, was used as a comparative Fab fragment. M5A-Fab bound to DFO via a linker (referred to as M5A-Fab-DFO) was prepared by use of the method described in Example 2.

The analysis by SPR was conducted using Biacore T200 (GE Healthcare Japan Corp.). 10 µg/mL human CEACAM5 (R&D Systems, Inc.) biotinylated with Biotin CAPture Kit, Series S (GE Healthcare Japan Corp.) and Biotin Labeling Kit-$NH_2$ (Dojindo Laboratories) was added to the surface of the sensor chip at a flow rate of 5 µL/min for 2 minutes, and immobilized thereonto. PB009-01, PB009-02, M5A-Fab and M5A-Fab-DFO were diluted with HBS-EP+ solution (GE Healthcare Japan Corp.) into 6 series at a 2-fold ratio from 400 nM, and 100 µL each was added to the channel at a flow rate of 50 µL/min. In this measurement system, the dissociation constant ($K_D$) of PB009-01, PB009-02, M5A-Fab or M5A-Fab-DFO for human CEACAM5 was calculated using data analysis software (BIA Evaluation, GE Healthcare Japan Corp.). As a result, as shown in the table given below, the binding activity of M5A-Fab was attenuated by the binding of DFO, whereas the binding activity of PB009-01 was not attenuated by the binding of DFO.

TABLE 1

| Fab | $K_D(M)$ | Fab bound to DFO | $K_D(M)$ |
|---|---|---|---|
| PB009-01 | 1.7E-10 | PB009-02 | 6.1E-10 |
| M5A-Fab | 1.6E-10 | M5A-Fab-DFO | 9.6E-09 |

Example 4: $^{89}$Zr Labeling of Conjugate of Fab Fragment Bound to DFO $^{89}$Zr was purchased as Zr-Oxalate from 3D Imaging LLC. 20 µL of Zr-Oxalate (2.6 mCi) was neutralized with 10 µL of 2 M sodium carbonate. Then, 20 µL of 5 mg/mL gentisic acid was added thereto. Further, 110 µL of 20 mM HEPES (4-(2-hydroxyethyl)-1-piperazineethanesulfonic acid) containing 0.05% polysorbate 80 was added thereto. 40 µL of 10 mg/mL PB009-02 was added thereto and reacted at room temperature for 30 minutes and then further reacted at 37° C. for 30 minutes. After the reaction, PB009-02 labeled with $^{89}$Zr (designated as PB009-03) was purified using Amicon Ultra 10K-0.5 mL centrifugal filter (Merck Millipore).

Figure 1B:
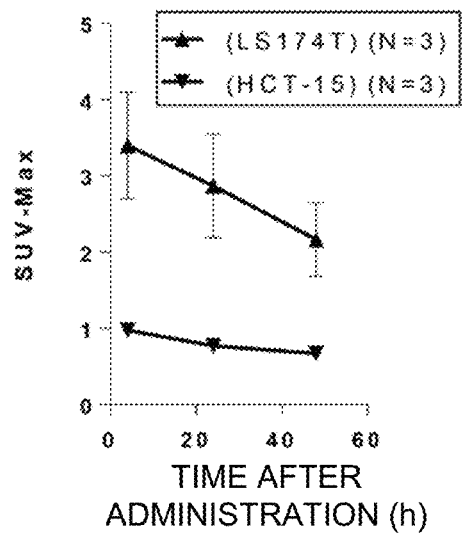
FIG. 1B is a graph showing results of analyzing images taken by PET 4 hours, 24 hours and 48 hours after administration of PB009-03 to a mouse in which human colorectal cancer cell line LS174T cells (human CEACAM5-positive cells) were subcutaneously transplanted to the right shoulder while human colorectal cancer cell line HCT-15 cells (human CEACAM5-negative cells) were subcutaneously transplanted to the left shoulder. The ordinate depicts a SUV-Max value of PB009-03 that accumulated in a tumor site. The error bars in the graph depict mean±standard deviation (mean±SEM).

Example 5: Contrast Evaluation of Conjugate in Subcutaneous Xenograft Model $1 \times 10^6$ human colorectal cancer cell line LS174T cells (ATCC®; CL-188) were subcutaneously xenografted as human CEACAM5-positive cells to the right shoulder of an immunodeficient mouse (NOG mouse; Taconic Biosciences), and $5 \times 10^6$ human colorectal cancer cell line HCT-15 cells (ATCC®; CCL-225) were subcutaneously xenografted as human CEACAM5-negative cells to the left shoulder. This Example was carried out at N=3. After the tumor volume reached approximately 300 $mm^3$, PB009-03 (approximately 20 µg, approximately 120 µCO was intravenously administered thereto. Photographs were taken by PET 4 hours, 24 hours and 48 hours after the administration of PB009-03, and SUV-Max of the tumor site was measured. As a result, as shown in FIG. 1A, PB009-03 was shown to accumulate in the LS174T cells (human CEACAM5-positive cells) more than in the HCT-15 cells (human CEACAM5-negative cells) 4 hours after the administration. As shown in FIG. 1B, PB009-03 was found to permit detection of human CEACAM5-positive cancer cells from 4 hours to 48 hours after the administration.

Figure 2A:
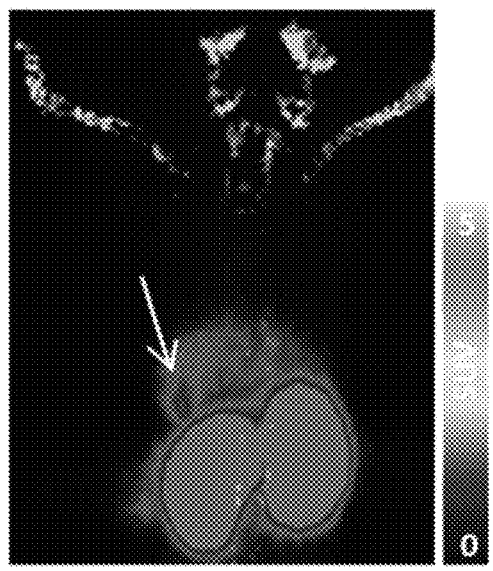
FIG. 2A is a representative image taken by PET 4 hours after administration of PB009-03 to a mouse in which luciferase-expressing LS174T cells (human CEACAM5-positive cells) were transplanted to the liver. The arrow depicts a cell-transplanted site. The right bar depicts a SUV-Max value.
Figure 2B:
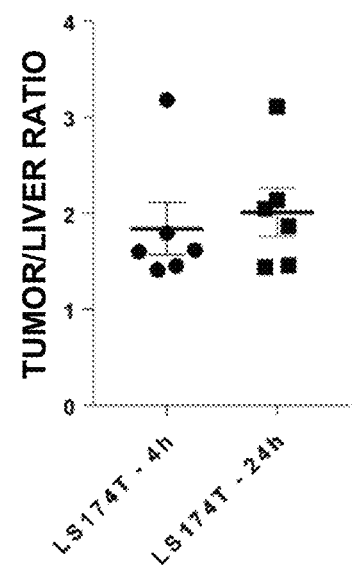
FIG. 2B is a graph showing results of analyzing images taken by PET 4 hours and 24 hours after administration of PB009-03 to a mouse in which luciferase-expressing LS174T cells (human CEACAM5-positive cells) were transplanted to the liver. The ordinate depicts a ratio between SUV-Max values of PB009-03 that accumulated in the liver and a tumor site (tumor/liver ratio). The error bars in the graph depict mean±standard deviation (mean±SEM).

Example 6: Contrast Evaluation of Conjugate in Hepatic Transplantation Model $1 \times 10^6$ luciferase-expressing LS174T cells were transplanted to the liver of an immunodeficient mouse (NSG mouse; The Jackson Laboratory) under anesthesia. This Example was carried out at N=6. The engraftment of the cells in the liver was confirmed with the expression of luciferase as an index using IVIS imaging system (PerkinElmer, Inc.). Then, PB009-03 (approximately 14 µg, approximately 100 µCi) prepared in the same way as in Example 4 was intravenously administered thereto. Photographs were taken by PET 4 hours and 24 hours after the administration of PB009-03. SUV-Max of the liver and LS174T tumor (which refers to a state where the transplanted LS174T cells were engrafted in the liver) was measured to calculate the ratio of SUV-Max of the tumor to SUV-Max of the liver. As a result, as shown in FIG. 2A, PB009-03 was shown to accumulate in the LS174T tumor engrafted in the liver 4 hours after the administration. The signal ratios of the tumor to the liver 4 hours and 24 hours after the administration were the values shown in FIG. 2B. From these, PB009-03 was found to permit detection of human CEACAM5-positive cancer cells present in the liver 4 hours and 24 hours after the administration.

INDUSTRIAL APPLICABILITY

The anti-human CEACAM5 antibody Fab fragment of the present invention and the conjugate comprising the anti-human CEACAM5 antibody Fab fragment are expected to be useful in the diagnosis of a cancer selected from the group consisting of colorectal cancer, breast cancer, lung cancer, thyroid gland cancer and a cancer resulting from the metastasis thereof.

SEQUENCE LISTING FREE TEXT

The numerical subtitle <223> in the sequence listing given below will describe "Artificial Sequence". Specifically, the nucleotide sequences represented by SEQ ID NOs: 1 and 3 of the sequence listing are the nucleotide sequences of the heavy chain fragment and the light chain, respectively, of PB009-01. The amino acid sequences represented by SEQ ID NOs: 2 and 4 are the amino acid sequences of the heavy chain fragment and the light chain encoded by SEQ ID NOs: 1 and 3, respectively.

The invention claimed is:

1. An anti-human CEACAM5 antibody Fab fragment selected from the group consisting of the following (a) and (b):
    (a) an anti-human CEACAM5 antibody Fab fragment comprising a heavy chain fragment comprising a heavy chain variable region consisting of an amino acid sequence from amino acid positions 1 to 121 of SEQ ID NO: 2 and a light chain comprising a light chain variable region consisting of an amino acid sequence from amino acid positions 1 to 112 of SEQ ID NO: 4; and
    (b) an anti-human CEACAM5 antibody Fab fragment comprising a heavy chain fragment comprising a heavy chain variable region derived from a heavy chain variable region consisting of an amino acid sequence from amino acid positions 1 to 121 of SEQ ID NO: 2 by the modification of glutamic acid at amino acid position 1 of SEQ ID NO: 2 into pyroglutamic acid, and a light chain comprising a light chain variable region consisting of an amino acid sequence from amino acid positions 1 to 112 of SEQ ID NO: 4.

2. The anti-human CEACAM5 antibody Fab fragment according to claim 1 selected from the group consisting of the following (a) and (b):
    (a) an anti-human CEACAM5 antibody Fab fragment comprising a heavy chain fragment consisting of the amino acid sequence represented by SEQ ID NO: 2 and a light chain consisting of the amino acid sequence represented by SEQ ID NO: 4; and
    (b) an anti-human CEACAM5 antibody Fab fragment comprising a heavy chain fragment derived from a heavy chain fragment consisting of the amino acid sequence represented by SEQ ID NO: 2 by the modification of glutamic acid at amino acid position 1 of SEQ ID NO: 2 into pyroglutamic acid, and a light chain consisting of the amino acid sequence represented by SEQ ID NO: 4.

3. The anti-human CEACAM5 antibody Fab fragment according to claim 2, comprising a heavy chain fragment consisting of the amino acid sequence represented by SEQ ID NO: 2 and a light chain consisting of the amino acid sequence represented by SEQ ID NO: 4.

4. A conjugate comprising a labeling moiety and an anti-human CEACAM5 antibody Fab fragment according to any one of claims 1 to 3.

5. The conjugate according to claim 4, wherein the labeling moiety is (i) a ligand and a linker, (ii) a ligand, (iii) a fluorescent dye and a linker, or (iv) a fluorescent dye.

6. The conjugate according to claim 5, wherein the labeling moiety is (i) a ligand and a linker, or (ii) a ligand.

7. The conjugate according to claim 6, wherein the ligand is a ligand represented by the following formula (A):

[Chemical Formula 1]

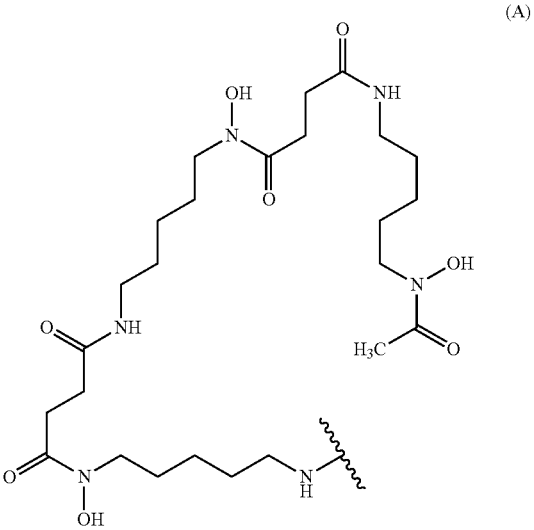

(A)

wherein the wavy line represents binding to the anti-human CEACAMS antibody Fab fragment or the linker.

8. The conjugate according to claim 6, wherein the labeling moiety is (i) a ligand and a linker, wherein the ligand and the linker are a group represented by the following formula (A'):

[Chemical Formula 2]

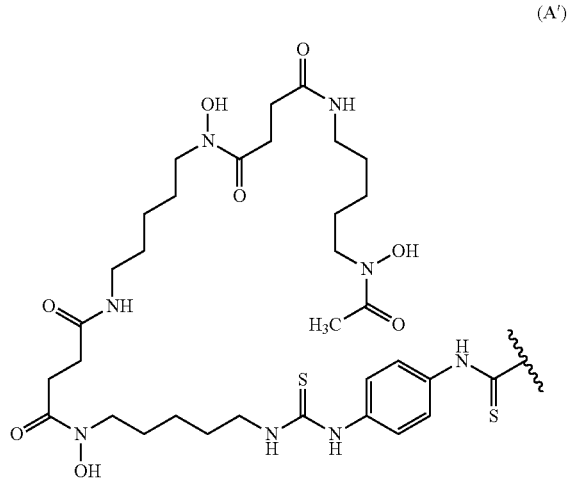

(A')

wherein the wavy line represents binding to the anti-human CEACAM5 antibody Fab fragment.

9. The conjugate according to claim 8, wherein the anti-human CEACAM5 antibody Fab fragment is bound to the carbon atom of a labeling moiety terminal C(=S) group via an amino group in the Fab fragment.

10. The conjugate according to claim 6 represented by the following formula (I):

(L-X)$_p$-Ab wherein Ab is the anti-human CEACAM5 antibody Fab fragment;
L is the ligand;
X is the linker or a bond; and
p is a natural number of 1 to 25.

11. The conjugate according to claim 10, wherein L is a ligand represented by the following formula (A):

[Chemical Formula 3]

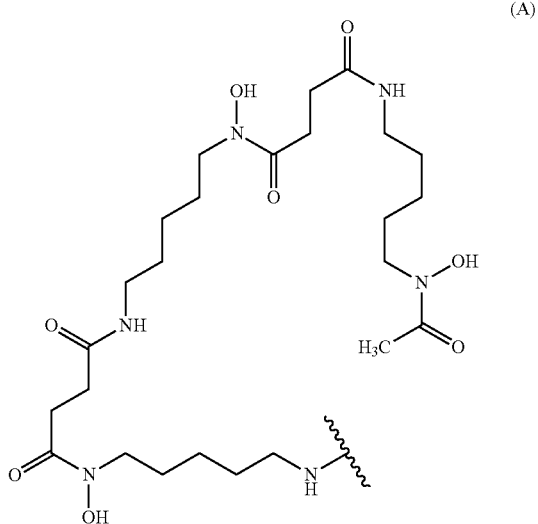

(A)

wherein the wavy line represents binding to X or Ab when X is a bond.

12. The conjugate according to claim 8 represented by the following formula (II):

[Chemical Formula 4]

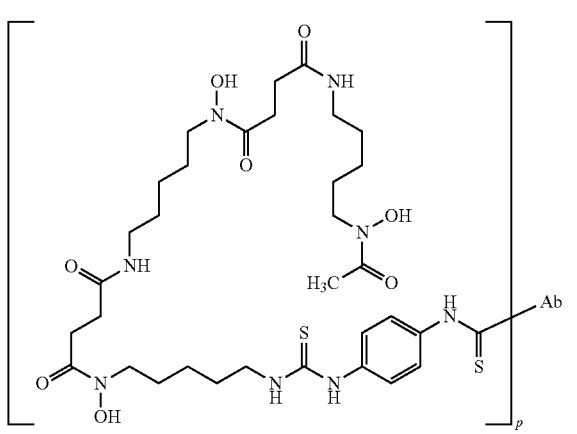

(II)

wherein Ab is the anti-human CEACAM5 antibody Fab fragment; and p is a natural number of 1 to 25, wherein Ab is bound to the carbon atom of labeling moiety terminal C(=S) via an amino group in the Ab.

13. The conjugate according to claim 10, wherein p is a natural number of 1 to 16.

14. The conjugate according to claim 10, wherein p is a natural number of 1 to 10.

15. The conjugate according to claim 5, further comprising a metal.

16. The conjugate according to claim 15, wherein the metal is a metal radioisotope.

17. The conjugate according to claim 15, wherein the metal is $^{89}$Zr.

18. The conjugate according to claim 16 or 17 which is a PET tracer.

19. A polynucleotide selected from the group consisting of the following (a) and (b):
(a) a polynucleotide comprising a nucleotide sequence encoding the heavy chain fragment of anti-human CEACAM5 antibody Fab fragment (a) according to claim 1; and
(b) a polynucleotide comprising a nucleotide sequence encoding the light chain of anti-human CEACAM5 antibody Fab fragment (a) according to claim 1.

20. A polynucleotide selected from the group consisting of the following (a) and (b):
(a) a polynucleotide comprising a nucleotide sequence encoding the heavy chain fragment of an anti-human CEACAM5 antibody Fab fragment according to claim 3; and
(b) a polynucleotide comprising a nucleotide sequence encoding the light chain of the anti-human CEACAM5 antibody Fab fragment according to claim 3.

21. An expression vector comprising the following (a) and/or (b):
(a) a polynucleotide comprising a nucleotide sequence encoding the heavy chain fragment of anti-human CEACAM5 antibody Fab fragment (a) according to claim 1; and
(b) a polynucleotide comprising a nucleotide sequence encoding the light chain of anti-human CEACAM5 antibody Fab fragment (a) according to claim 1.

22. An expression vector comprising the following (a) and/or (b):
(a) a polynucleotide comprising a nucleotide sequence encoding the heavy chain fragment of an anti-human CEACAM5 antibody Fab fragment according to claim 3; and
(b) a polynucleotide comprising a nucleotide sequence encoding the light chain of the anti-human CEACAM5 antibody Fab fragment according to claim 3.

23. A host cell selected from the group consisting of the following (a) to (d):
(a) a host cell transformed with an expression vector comprising a polynucleotide comprising a nucleotide sequence encoding the heavy chain fragment of anti-human CEACAM5 antibody Fab fragment (a) according to claim 1;
(b) a host cell transformed with an expression vector comprising a polynucleotide comprising a nucleotide sequence encoding the light chain of anti-human CEACAM5 antibody Fab fragment (a) according to claim 1;
(c) a host cell transformed with an expression vector comprising a polynucleotide comprising a nucleotide sequence encoding the heavy chain fragment of anti-human CEACAM5 antibody Fab fragment (a) according to claim 1 and a polynucleotide comprising a nucleotide sequence encoding the light chain of anti-human CEACAM5 antibody Fab fragment (a) according to claim 1; and
(d) a host cell transformed with an expression vector comprising a polynucleotide comprising a nucleotide sequence encoding the heavy chain fragment of anti-human CEACAM5 antibody Fab fragment (a) according to claim 1 and an expression vector comprising a polynucleotide comprising a nucleotide sequence encoding the light chain of anti-human CEACAM5 antibody Fab fragment (a) according to claim 1.

24. A host cell selected from the group consisting of the following (a) to (d):
(a) a host cell transformed with an expression vector comprising a polynucleotide comprising a nucleotide sequence encoding the heavy chain fragment of an anti-human CEACAM5 antibody Fab fragment according to claim 3;
(b) a host cell transformed with an expression vector comprising a polynucleotide comprising a nucleotide sequence encoding the light chain of the anti-human CEACAM5 antibody Fab fragment according to claim 3;
(c) a host cell transformed with an expression vector comprising a polynucleotide comprising a nucleotide sequence encoding the heavy chain fragment of the anti-human CEACAM5 antibody Fab fragment according to claim 3 and a polynucleotide comprising a nucleotide sequence encoding the light chain of the anti-human CEACAM5 antibody Fab fragment according to claim 3; and
(d) a host cell transformed with an expression vector comprising a polynucleotide comprising a nucleotide sequence encoding the heavy chain fragment of the anti-human CEACAM5 antibody Fab fragment according to claim 3 and an expression vector comprising a polynucleotide comprising a nucleotide sequence encoding the light chain of the anti-human CEACAM5 antibody Fab fragment according to claim 3.

25. A method for producing an anti-human CEACAM5 antibody Fab fragment, comprising the step of culturing a host cell selected from the group consisting of the following (a) to (c) to express the anti-human CEACAM5 antibody Fab fragment:
(a) a host cell transformed with an expression vector comprising a polynucleotide comprising a nucleotide sequence encoding the heavy chain fragment of anti-human CEACAM5 antibody Fab fragment (a) according to claim 1 and a polynucleotide comprising a nucleotide sequence encoding the light chain of anti-human CEACAM5 antibody Fab fragment (a) according to claim 1;
(b) a host cell transformed with an expression vector comprising a polynucleotide comprising a nucleotide sequence encoding the heavy chain fragment of anti-human CEACAM5 antibody Fab fragment (a) according to claim 1 and an expression vector comprising a polynucleotide comprising a nucleotide sequence encoding the light chain of anti-human CEACAM5 antibody Fab fragment (a) according to claim 1; and
(c) a host cell transformed with an expression vector comprising a polynucleotide comprising a nucleotide sequence encoding the heavy chain fragment of anti-human CEACAM5 antibody Fab fragment (a) according to claim 1, and a host cell transformed with an expression vector comprising a polynucleotide comprising a nucleotide sequence encoding the light chain of anti-human CEACAM5 antibody Fab fragment (a) according to claim 1.

26. A method for producing an anti-human CEACAM5 antibody Fab fragment, comprising the step of culturing a host cell selected from the group consisting of the following (a) to (c) to express the anti-human CEACAM5 antibody Fab fragment:
(a) a host cell transformed with an expression vector comprising a polynucleotide comprising a nucleotide sequence encoding the heavy chain fragment of an anti-human CEACAM5 antibody Fab fragment according to claim 3 and a polynucleotide comprising a nucleotide sequence encoding the light chain of the anti-human CEACAM5 antibody Fab fragment according to claim 3;
(b) a host cell transformed with an expression vector comprising a polynucleotide comprising a nucleotide sequence encoding the heavy chain fragment of the anti-human CEACAM5 antibody Fab fragment according to claim 3 and an expression vector comprising a polynucleotide comprising a nucleotide sequence encoding the light chain of the anti-human CEACAM5 antibody Fab fragment according to claim 3; and
(c) a host cell transformed with an expression vector comprising a polynucleotide comprising a nucleotide sequence encoding the heavy chain fragment of the anti-human CEACAM5 antibody Fab fragment according to claim 3, and a host cell transformed with an expression vector comprising a polynucleotide comprising a nucleotide sequence encoding the light chain of the anti-human CEACAM5 antibody Fab fragment according to claim 3.

27. A method for producing a conjugate comprising a labeling moiety and an anti-human CEACAM5 antibody Fab fragment, comprising the steps of: preparing the anti-human CEACAM5 antibody Fab fragment by a method according to claim 25 or 26; and covalently binding the Fab fragment to the labeling moiety.

28. A method for producing a conjugate comprising a ligand and an anti-human CEACAM5 antibody Fab fragment, comprising the steps of: preparing the anti-human CEACAM5 antibody Fab fragment by a method according to claim 25 or 26; and covalently binding the Fab fragment to the ligand via a linker or directly.

29. A method for producing a conjugate comprising a labeling moiety labeled with a metal radioisotope and an anti-human CEACAM5 antibody Fab fragment, comprising the steps of: producing a conjugate comprising a ligand and an anti-human CEACAM5 antibody Fab fragment by a method according to claim 28; and binding the metal radioisotope to the ligand of the conjugate through a coordinate bond.

30. A composition for diagnosis comprising a conjugate according to claim 15, and a pharmaceutically acceptable carrier.

31. The composition for diagnosis according to claim 30 which is a clinical staging drug.

32. A method for diagnosing a cancer selected from colorectal cancer, breast cancer, lung cancer, thyroid gland cancer or a cancer resulting from the metastasis thereof, comprising administering a conjugate according to claim 15 to a subject.

33. The method according to claim 32, wherein the cancer is colorectal cancer or a cancer resulting from the metastasis of colorectal cancer.

34. The method according to claim 33, wherein the cancer resulting from the metastasis of colorectal cancer is metastatic liver cancer.

35. The conjugate according to claim 12, wherein p is a natural number of 1 to 10 and the conjugate further comprises a metal and the metal is $_{89}$Zr.

* * * * *